(12) United States Patent
Morita et al.

(10) Patent No.: US 12,315,134 B2
(45) Date of Patent: May 27, 2025

(54) REINFORCED CONCRETE STRUCTURE EVALUATING DEVICE, METHOD, AND PROGRAM

(71) Applicant: GEO SEARCH CO., LTD., Tokyo (JP)

(72) Inventors: Hideaki Morita, Tokyo (JP); Yoko Taki, Tokyo (JP); Yukio Ozawa, Tokyo (JP)

(73) Assignee: GEO SEARCH CO., LTD., Tokyo (JP)

( * ) Notice: Subject to any disclaimer, the term of this patent is extended or adjusted under 35 U.S.C. 154(b) by 945 days.

(21) Appl. No.: 17/432,340

(22) PCT Filed: Feb. 26, 2020

(86) PCT No.: PCT/JP2020/007648
§ 371 (c)(1),
(2) Date: Mar. 14, 2022

(87) PCT Pub. No.: WO2020/175528
PCT Pub. Date: Sep. 3, 2020

(65) Prior Publication Data
US 2022/0230290 A1 Jul. 21, 2022

(30) Foreign Application Priority Data
Feb. 26, 2019 (JP) .................. 2019-033202

(51) Int. Cl.
*G06T 7/00* (2017.01)
*G01N 33/38* (2006.01)

(52) U.S. Cl.
CPC ........... *G06T 7/001* (2013.01); *G01N 33/383* (2013.01); *G06T 2207/30184* (2013.01)

(58) Field of Classification Search
CPC ................ G06T 7/001; G06T 7/0004; G06T 2207/30184; G06T 2207/30132; G01N 33/383; G01N 22/02; E01D 22/00
See application file for complete search history.

(56) References Cited

U.S. PATENT DOCUMENTS 6,429,802 B1 * 8/2002 Roberts .................... G01V 3/12
342/195
6,772,091 B1 * 8/2004 Roberts ................ G01N 23/223
342/118
(Continued)

FOREIGN PATENT DOCUMENTS

CN 107063988 A 8/2017
CN 108076657 A 5/2018
(Continued)

OTHER PUBLICATIONS

International Search Report and Written Opinion for Application No. PCT/JP2020/007648, dated May 26, 2020.
Office Action for Taiwan Application, dated Aug. 23, 2023.

*Primary Examiner* — John B Strege
(74) *Attorney, Agent, or Firm* — MARSHALL, GERSTEIN & BORUN LLP

(57) ABSTRACT

An acquisition section (12) acquires a reflected wave intensity image in which a reflected wave intensity of an electromagnetic wave that has been radiated in a direction through a surface of a reinforced concrete structure toward an interior of the reinforced concrete structure at respective positions on the surface of the reinforced concrete structure is expressed by pixel values of pixels corresponding to each of the respective positions. A setting section (14) sets an evaluation target range in the acquired reflected wave intensity image. A computation section (16) computes a statistical indicator of a type set according to the set range for pixel values in the reflected wave intensity image. An evaluation section (18) evaluates a degree of deterioration of the reinforced concrete structure using the computed values.

11 Claims, 25 Drawing Sheets

(56) References Cited

U.S. PATENT DOCUMENTS

| | | | | |
|---|---|---|---|---|
| 7,075,315 B2* | 7/2006 | Tanaka | ................. | G01N 33/383 |
| | | | | 324/642 |
| 10,175,350 B1 | 1/2019 | Tsokos et al. | | |
| 10,794,990 B2* | 10/2020 | Takamine | ............ | G01N 33/383 |
| 2012/0280849 A1* | 11/2012 | Chang | ..................... | G01V 3/12 |
| | | | | 342/22 |
| 2015/0115980 A1* | 4/2015 | Bulumulla | ........... | G01N 29/265 |
| | | | | 324/642 |
| 2017/0269204 A1 | 9/2017 | Takamine et al. | | |
| 2020/0284576 A1* | 9/2020 | Chaudhury | ........... | G06T 7/0004 |
| 2023/0366870 A1* | 11/2023 | Luloff | ..................... | G01B 7/12 |

FOREIGN PATENT DOCUMENTS

| | | |
|---|---|---|
| JP | 2001-165870 A | 6/2001 |
| JP | 2012-184624 A | 9/2012 |
| JP | 2015-215332 A | 12/2015 |
| JP | 62-61797 B1 | 1/2018 |
| JP | 2018-004598 A | 1/2018 |
| JP | 2019-033202 A | 2/2019 |

* cited by examiner

FIG.9
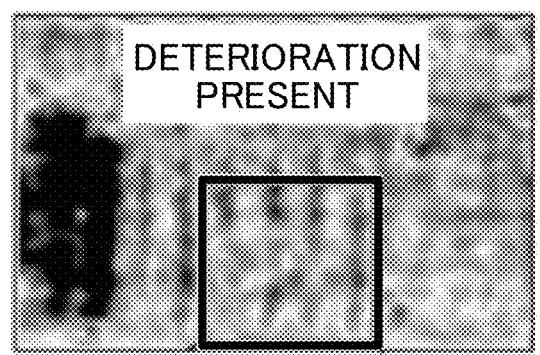
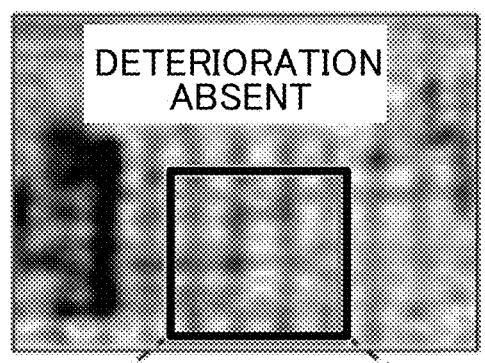
STANDARD DEVIATIONS
(MEDIAN VALUE: 3.9)
STANDARD DEVIATIONS
(MEDIAN VALUE: 10.0)

FIG.14

| CONDITION | EVALUATION RANGE | STANDARD DEVIATION | AVERAGE VALUE |
|---|---|---|---|
| SOUND STEEL REINFORCEMENT LOCATION | 1 | 9.4 | 41.5 |
| CORRODED STEEL REINFORCEMENT LOCATION | 2 | 4.1 | 7.9 |
| SOUND CONCRETE LOCATION | 3 | 3.2 | 11.5 |

FIG.17
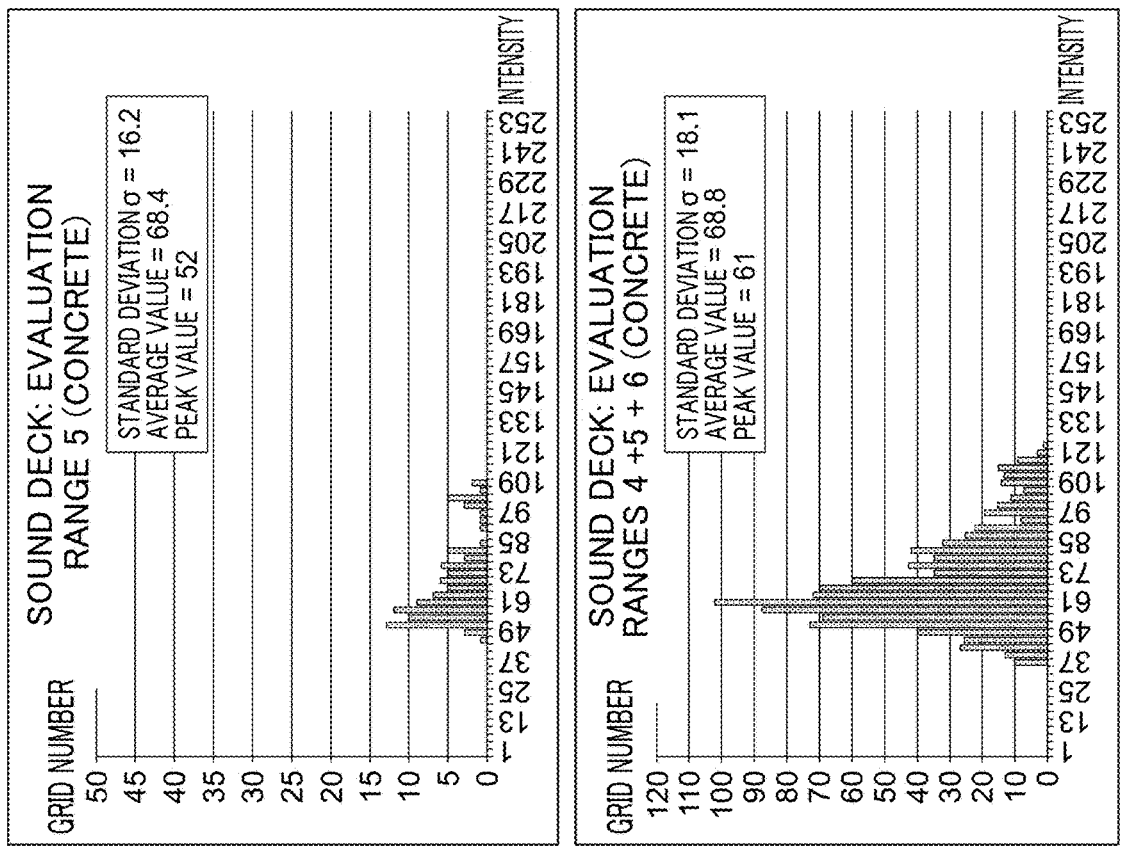
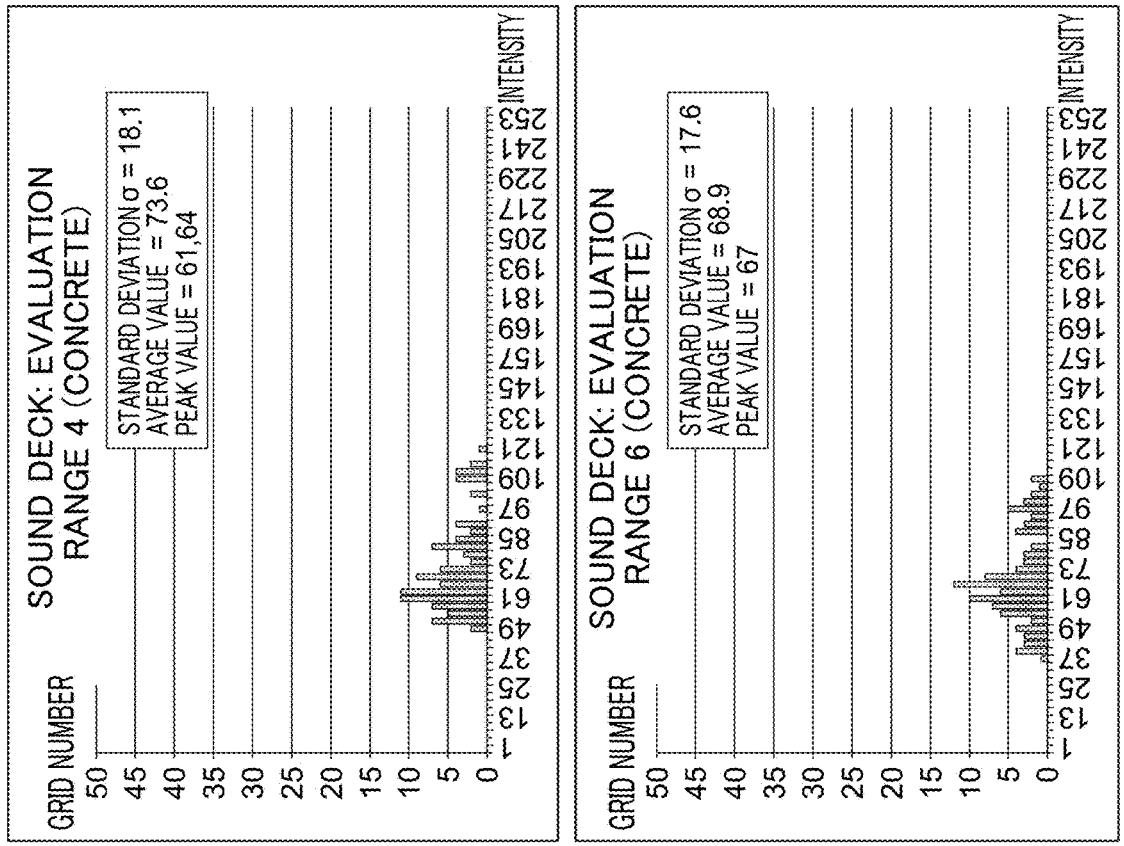

FIG.18

| CONDITION | POSITION | EVALUATION RANGE | NUMBER OF SAMPLES | STANDARD DEVIATION | AVERAGE VALUE | PEAK |
|---|---|---|---|---|---|---|
| SOUND DECK | STEEL REINFORCEMENT | 1 | 100 | 45.9 | 137.8 | 133 |
| | | 2 | 100 | 35.4 | 166.2 | 178 |
| | | 3 | 100 | 32.5 | 146.7 | 136 |
| | | 1 + 2 + 3 | 300 | 40.2 | 150.2 | 136 |
| | CONCRETE | 4 | 100 | 18.1 | 73.6 | 63 |
| | | 5 | 100 | 16.2 | 68.4 | 52 |
| | | 6 | 100 | 17.6 | 68.9 | 67 |
| | | 4 + 5 + 6 + OTHER 7 CASES | 1000 | 18.1 | 68.8 | 61 |

FIG.25

| condition | position | evaluation range | number of samples | standard deviation | average value | peak |
|---|---|---|---|---|---|---|
| honeycombed deck | steel reinforcement | 1 | 100 | 28.4 | 51.7 | 55 |
| | | 2 | 100 | 25.8 | 58.5 | 49 |
| | | 3 | 100 | 32.4 | 54.0 | 52 |
| | | 1 + 2 + 3 | 300 | 29.1 | 54.8 | 49 |
| | concrete | 4 | 100 | 17.0 | 47.1 | 22 |
| | | 5 | 100 | 17.9 | 46.9 | 49 |
| | | 6 | 100 | 19.5 | 49.9 | 42 |
| | | 4 + 5 + 6 | 300 | 18.2 | 48 | 49 |
| honeycombed deck + 1 mm pooled water | steel reinforcement | 1 | 100 | 21.1 | 44.1 | 43 |
| | | 2 | 100 | 19.6 | 45.6 | 58 |
| | | 3 | 100 | 28.7 | 55.0 | 49 |
| | | 1 + 2 + 3 | 300 | 24.0 | 48.2 | 58 |
| | concrete | 4 | 100 | 13.4 | 28.1 | 13,25 |
| | | 5 | 100 | 14.5 | 26.5 | 16 |
| | | 6 | 100 | 14.6 | 31.8 | 34 |
| | | 4 + 5 + 6 | 300 | 14.3 | 28.8 | 16,25 |
| honeycombed deck + 3 mm pooled water | steel reinforcement | 1 | 100 | 21.2 | 58.7 | 43 |
| | | 2 | 100 | 29.8 | 51.3 | 34 |
| | | 3 | 100 | 15.0 | 33.7 | 19 |
| | | 1 + 2 + 3 | 300 | 25.1 | 47.9 | 43 |
| | concrete | 4 | 100 | 21.8 | 49.2 | 52 |
| | | 5 | 100 | 20.0 | 46.3 | 31 |
| | | 6 | 100 | 26.6 | 39.4 | 28,34 |
| | | 4 + 5 + 6 | 300 | 23.3 | 44.9 | 31 |

REINFORCED CONCRETE STRUCTURE EVALUATING DEVICE, METHOD, AND PROGRAM

FIELD

Technology disclosed herein relates to a reinforced concrete structure evaluation device, method, and program, and in particular to a reinforced concrete structure evaluation device, method, and program for evaluating a degree of deterioration within a reinforced concrete structure.

BACKGROUND ART

Hitherto, image diagnostics employing electromagnetic waves have been employed to evaluate the degree of deterioration within a reinforced concrete deck configuring a road surface structure of a road bridge.

For example, a method has been proposed for surveying damage to a steel deck pavement by radiating an electromagnetic wave from above a survey object surface to below the survey object surface, and detecting multiple reflected wave data of this electromagnetic wave. Even after a detection timing of a first steel deck reflected wave has passed, a reflected wave detected after a duration corresponding to a total travel path length of the reflected wave has elapsed is regarded as a reflected wave from a surface at a virtual survey depth, or a through-pavement wave that has passed along the travel path. Noise is removed from the observed waves by performing background subtraction processing for each virtual depth, enabling damaged portions to be observed in isolation. In addition, a maximum value of the intensity of the reflected waves detected at each of plural different virtual depths is set as an overlay processing value, and damaged pavement locations are displayed and expressed according to damage levels in an overlaid horizontal surface image created from the reflected wave intensities after the overlay processing (see, for example, Japanese Patent Application Laid-Open (JP-A) No. 2015-215332).

SUMMARY OF INVENTION

Technical Problem

However, the image diagnostics employed in conventional technology require a special expert to look at an image and determine sound portions and deteriorated portions of a reinforced concrete deck in relative terms. Qualitative evaluation such as this is difficult to interpret without specialist technical knowledge.

In consideration of the above circumstances, an object of technology disclosed herein is to provide a reinforced concrete structure evaluation device, method, and program that enables quantitative evaluation of a degree of deterioration in a reinforced concrete structure interior.

Solution to Problem

In order to realize the objectives described above, a reinforced concrete structure evaluation device according to technology disclosed herein is configured including an acquisition section configured to acquire an image in which a reflected wave intensity, of an electromagnetic wave that has been radiated in a direction through a surface of a reinforced concrete structure toward an interior of the reinforced concrete structure at respective positions on the surface of the reinforced concrete structure, is expressed by pixel values of pixels corresponding to each of the respective positions, a setting section configured to set an evaluation target range in the image acquired by the acquisition section, a computation section configured to compute a statistical indicator, of a type corresponding to the range set by the setting section, for pixel values in the image, and an evaluation section configured to evaluate a degree of deterioration of the reinforced concrete structure using values computed by the computation section.

In the reinforced concrete structure evaluation device according to technology disclosed herein, the acquisition section acquires an image in which the reflected wave intensity, of the electromagnetic wave that has been radiated in a direction through the surface of the reinforced concrete structure toward the interior of the reinforced concrete structure at respective positions on the surface of the reinforced concrete structure, is expressed by the pixel values of the pixels corresponding to each of the respective positions. The setting section sets the evaluation target range in the image acquired by the acquisition section. The computation section computes a statistical indicator of a type corresponding to the range set by the setting section, for the pixel values in the image. The evaluation section evaluates the degree of deterioration of the reinforced concrete structure using values computed by the computation section. This enables the degree of deterioration of the reinforced concrete structure interior to be quantitatively evaluated.

Moreover, configuration may be made wherein the setting section is configured to set a range including a region at which the presence of steel reinforcement is indicated and a region at which the presence of steel reinforcement is not indicated in the image acquired by the acquisition section, and the computation section is configured to compute as the statistical indicator a value representing a variation in pixel values in the range. This enables clear evaluation to be performed employing the value representing the variation in pixel values.

Moreover, configuration may be made wherein, in a case in which the setting section sets the range for plural locations in the image, the setting section sets plural of ranges such that the region at which the presence of steel reinforcement is indicated and the region at which the presence of steel reinforcement is not indicated are uniformly proportionate to each other in each of the plurality of ranges. This enables stable evaluation to be performed employing the values representing the variation in pixel values.

Moreover, configuration may be made wherein the setting section is configured to set, in the image, a plurality of ranges in a grid pattern, with one side of the grid pattern aligned with a direction along the region at which the presence of steel reinforcement is indicated. This enables the range setting to be performed efficiently.

Moreover, configuration may be made wherein the setting section is configured to set an interval between respective single sides of the ranges in the grid pattern so as to be equal to an interval between the regions at which the presence of steel reinforcement is indicated. This enables the range setting to be performed efficiently such that the region at which the presence of steel reinforcement is indicated and the region at which the presence of steel reinforcement is not indicated are in uniform proportions to each other.

Moreover, configuration may be made wherein the setting section is configured to set a range deemed to include only a region at which the presence of steel reinforcement is indicated, or a range deemed to include only a region at which the presence of steel reinforcement is not indicated in the image acquired by the acquisition section, and the computation section is configured to compute, as the statistical indicator, a value representing a variation in pixel values in the range and an average value of the pixel values. This enables detailed evaluation to be performed for the region at which the presence of steel reinforcement is indicated and the region at which the presence of steel reinforcement is not indicated respectively.

Moreover, configuration may be made wherein the evaluation section is configured to evaluate the degree of deterioration by comparing a value computed by the computation section against a predetermined reference value.

Moreover, configuration may be made wherein the evaluation section is configured to evaluate a change over time in the degree of deterioration by comparing against each other values computed by the computation section for each of plural of the images acquired over time for a single location on the reinforced concrete structure.

Moreover, configuration may be made wherein the evaluation section is configured to evaluate the degree of deterioration by comparing against each other values computed by the computation section for each of plural of the images acquired for different locations on the reinforced concrete structure.

Employing the statistical indicator computed for the pixel values in the manner described above enables quantitative evaluation of the degree of deterioration of the reinforced concrete structure interior in a variety of situations.

Moreover, a reinforced concrete structure evaluation method according to technology disclosed herein includes with an acquisition section, acquiring an image in which a reflected wave intensity of an electromagnetic wave that has been radiated in a direction through a surface of a reinforced concrete structure toward an interior of the reinforced concrete structure at respective positions on the surface of the reinforced concrete structure, is expressed by pixel values of pixels corresponding to each of the respective positions, with a setting section, setting an evaluation target range in the image acquired by the acquisition section, with a computation section, computing a statistical indicator, selected in accordance with the range set by the setting section for pixel values in the image, and with an evaluation section, evaluating a degree of deterioration of the reinforced concrete structure using values computed by the computation section.

Furthermore, a reinforced concrete structure evaluation program according to technology disclosed herein is a program configured to cause a computer to function as the respective sections configuring the reinforced concrete structure evaluation device described above.

Advantageous Effects of Invention

The reinforced concrete structure evaluation device, method, and program according to technology disclosed herein perform evaluation employing the statistical indicator of a type set according to the evaluation range set in the image expressed by pixel values corresponding to the intensity of reflected electromagnetic waves that have been radiated into a reinforced concrete structure, thereby enabling quantitative evaluation of a degree of deterioration in a reinforced concrete structure interior.

BRIEF DESCRIPTION OF DRAWINGS

FIG. 9 is a diagram to explain an example of degree of deterioration evaluation employing standard deviations.

FIG. 14 is a diagram illustrating standard deviations and average values of pixel values for respective evaluation ranges corresponding to a sound steel reinforcement location, a corroded steel reinforcement location, and a sound concrete location.

FIG. 17 is a diagram illustrating pixel value distributions in evaluation ranges corresponding to concrete portions in a sound deck.

FIG. 18 is a diagram illustrating standard deviations and average values of pixel values for respective evaluation ranges corresponding to a sound deck and a deck with corroded steel reinforcement.

FIG. 25 is a diagram illustrating pixel value distributions in evaluation ranges corresponding to a honeycombed deck, a honeycombed deck with 1 mm of pooled water, and a honeycombed deck with 3 mm of pooled water.

DESCRIPTION OF EMBODIMENTS

Explanation follows regarding examples of exemplary embodiments of technology disclosed herein, with reference to the drawings.

The exemplary embodiments described below employ examples in which evaluation is performed for a degree of deterioration in the interior of a reinforced concrete deck configuring a road surface structure on a road bridge.

First Exemplary Embodiment

Figure 1:
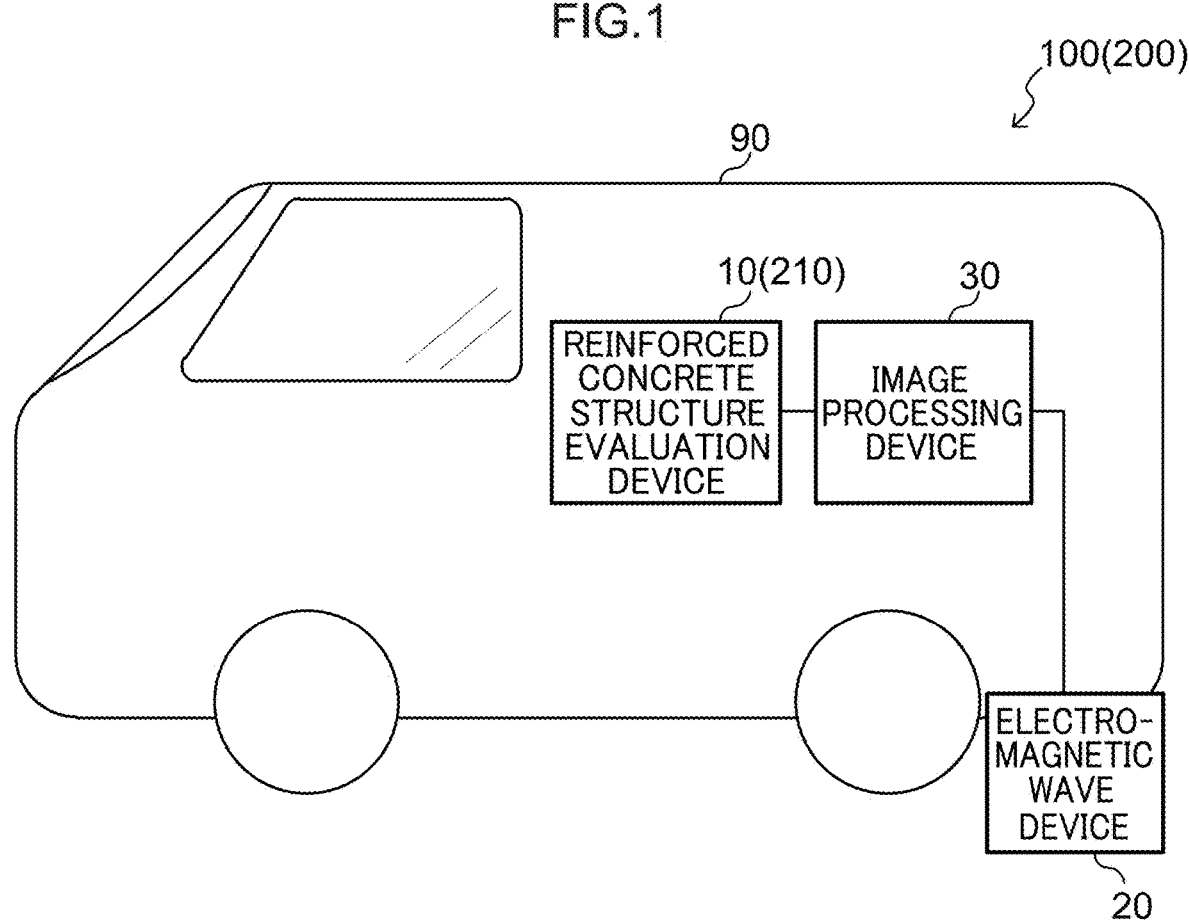
FIG. 1 is a diagram illustrating schematic configuration of a reinforced concrete structure evaluation system.

As illustrated in FIG. 1, a reinforced concrete structure evaluation system 100 according to a first exemplary embodiment is configured including a reinforced concrete structure evaluation device 10, an electromagnetic wave device 20, and an image processing device 30.

The electromagnetic wave device 20 includes plural linearly arrayed electromagnetic wave radiation elements and electromagnetic wave pick-up elements. The electromagnetic wave device 20 is, for example, provided at a rear lower section of a vehicle 90. A direction of progress of the vehicle 90 corresponds to a bridge axis direction, and the linear array direction of the electromagnetic wave device 20 is a direction at right angles to the bridge axis.

Figure 2:
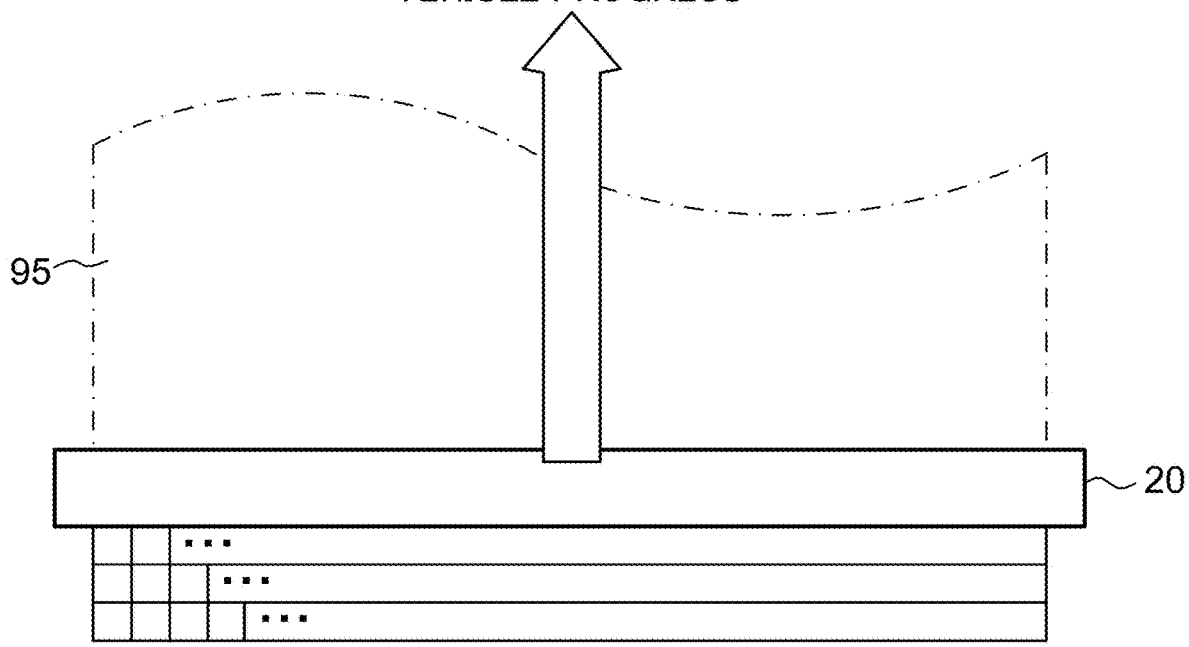
FIG. 2 is a diagram to explain detection of a reflected response waveform.
Figure 3:
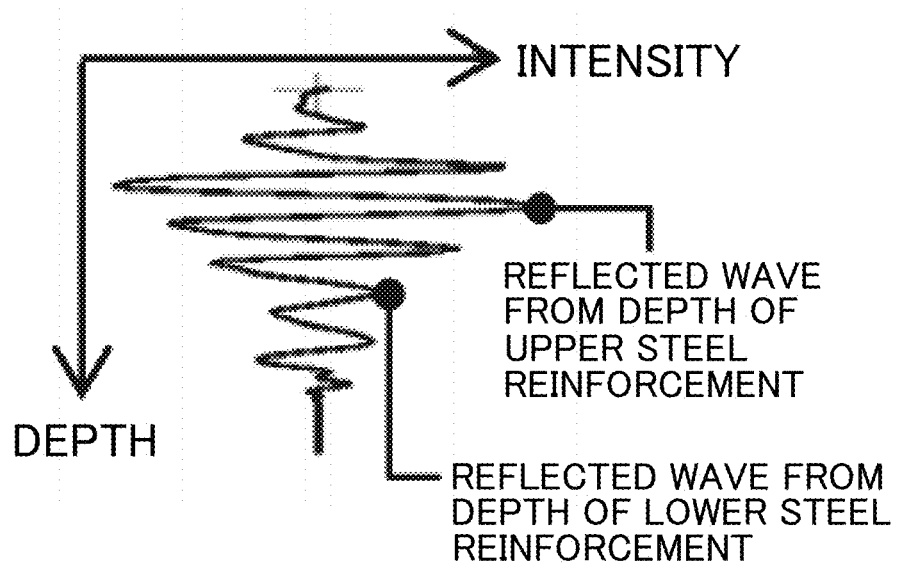
FIG. 3 is a diagram illustrating an example of a reflected response waveform detected for a single grid square.

As illustrated in FIG. 2, the electromagnetic wave device 20 radiates electromagnetic waves in a direction through the surface and into the interior of a reinforced concrete deck (a depth direction) and receives reflected waves while scanning a reflected wave intensity detection range 95 on the road bridge surface in the direction of vehicle movement. Reflected wave intensities are thus detected according to depth in respective grid squares of the reflected wave intensity detection range 95. The reflected wave intensities according to depth are detected based on reflected response waveforms in the respective grid squares, as illustrated in FIG. 3. As an example, each grid square measures 1 cm×1 cm, and the width of the one linear array is 2.0 m. In such a configuration, reflected response waveforms are detected for 200 grid squares on a single linear array.

The amount of time between radiation of an electromagnetic wave and reception of the reflected wave corresponds to the depth. As illustrated in FIG. 3, from the reflected response waveform, a reflected wave intensity can be obtained for each depth of the reinforced concrete deck by extracting a reflected wave intensity corresponding to each desired depth. Namely, a reflected response waveform is detected for each two-dimensional grid square set on the road bridge surface, and plural reflected wave intensity values are obtained with respect to the depth direction from the detected reflected response waveform. In this manner, reflected wave intensities are obtained in three dimensions for the reflected wave intensity detection range 95.

The electromagnetic wave device 20 outputs reflected response waveform information (reflected wave intensities according to depth) acquired for each grid square to the image processing device 30.

Note that the electromagnetic wave device 20 is not limited to a configuration attached to the vehicle 90, and the electromagnetic wave device 20 may be held by a worker, built into a handcart, or the like.

Figure 4:
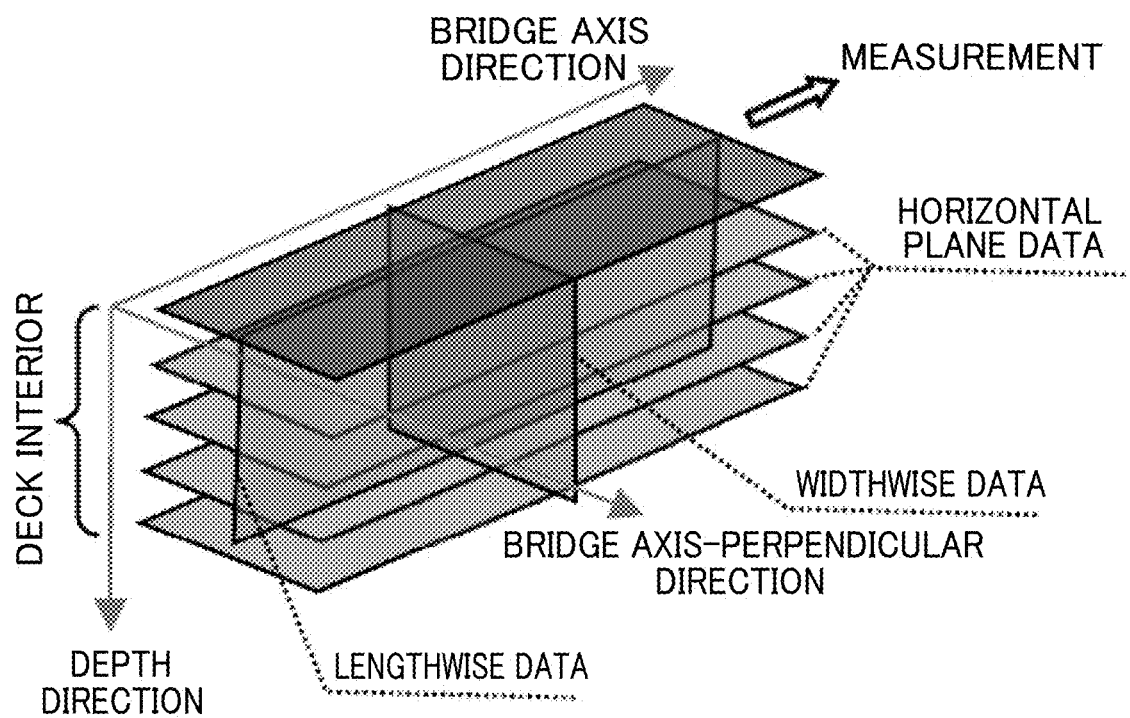
FIG. 4 is a diagram to explain reflected wave intensities in three dimensions.

The image processing device 30 extracts a reflected wave intensity for each desired depth from the reflected response waveform for each grid square output from the electromagnetic wave device 20, and converts these reflected wave intensities into pixel values, The image processing device 30 then generates reflected wave intensity images by performing planar processing to connect together pixels corresponding to the respective grid squares. As described above, the reflected response waveform information for the respective grid squares output from the electromagnetic wave device 20 expresses reflected wave intensities in three dimensions. As illustrated in FIG. 4, this information can be employed by the image processing device 30 to generate reflected horizontal reflected wave intensity images representing data in horizontal planes with respect to the depth direction, lengthwise reflected wave intensity images representing data in lengthwise planes following the bridge axis direction, and widthwise reflected wave intensity images representing data in widthwise planes following a direction at right angles to the bridge axis.

The image processing device 30 outputs the generated reflected wave intensity images.

Figure 5:
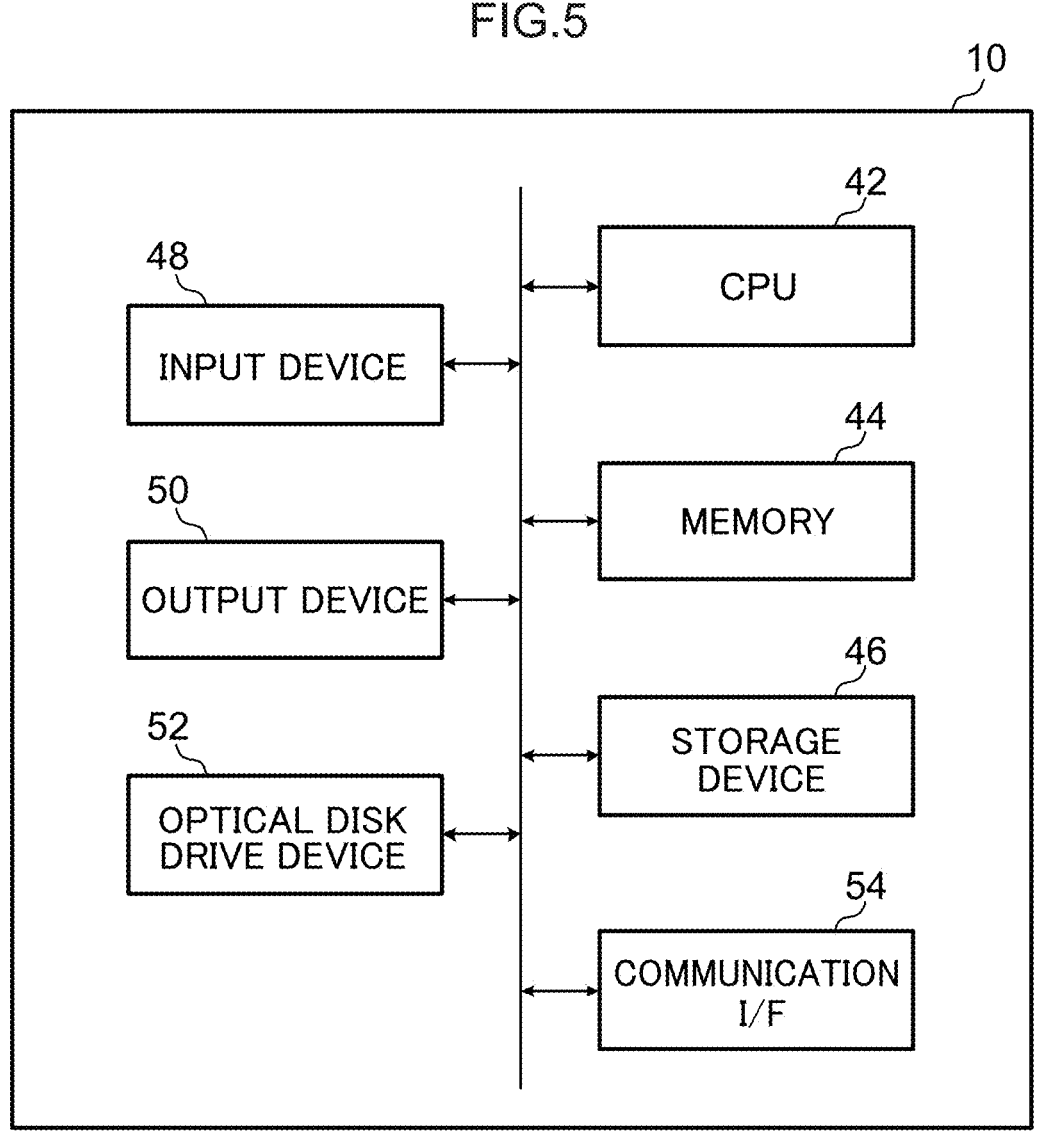
FIG. 5 is a block diagram illustrating a hardware configuration of a reinforced concrete structure evaluation device.

FIG. 5 is a block diagram illustrating a hardware configuration of the reinforced concrete structure evaluation device 10 according to the first exemplary embodiment. As illustrated in FIG. 5, the reinforced concrete structure evaluation device 10 includes a central processing unit (CPU) 42, memory 44, a storage device 46, an input device 48, an output device 50, an optical disk drive device 52, and a communication interface (I/F) 54. The respective configurations are connected together so as to be capable of communicating with each other through a bus.

The storage device 46 stores a reinforced concrete structure evaluation program for executing reinforced concrete structure evaluation processing. The CPU 42 is a central processing unit that executes various programs and controls various configurations. Namely, the CPU 42 reads the program from the storage device 46 and executes the program using the memory 44 as a workspace. The CPU 42 controls the various configurations and performs various arithmetic processing according to the program stored in the storage device 46.

The memory 44 is configured by random access memory (RAM), and serves as a workspace that temporarily stores programs and data. The storage device 46 is configured by read only memory (ROM) and a hard disk drive (HDD) or solid state drive (SSD), and stores various programs including an operating system, as well as various data.

The input device 48 is, for example, a device used to perform various input, such as a keyboard or a mouse. The output device 50 is, for example, a device used to output various information, such as a display or a printer. The functionality of the input device 48 and the output device 50 may be consolidated by employing a touch panel display as the output device 50. The optical disk drive device 52 reads data stored on various recording media such as compact disc read only memory (CD-ROM) or Blu-ray discs, and also writes data to such recording media.

The communication I/F 54 is an interface for communicating with other equipment, and may for example employ a protocol such as Ethernet (registered trademark), FDDI, or Wi-Fi (registered trademark).

Next, explanation follows regarding functional configuration of the reinforced concrete structure evaluation device 10 according to the first exemplary embodiment.

Figure 6:
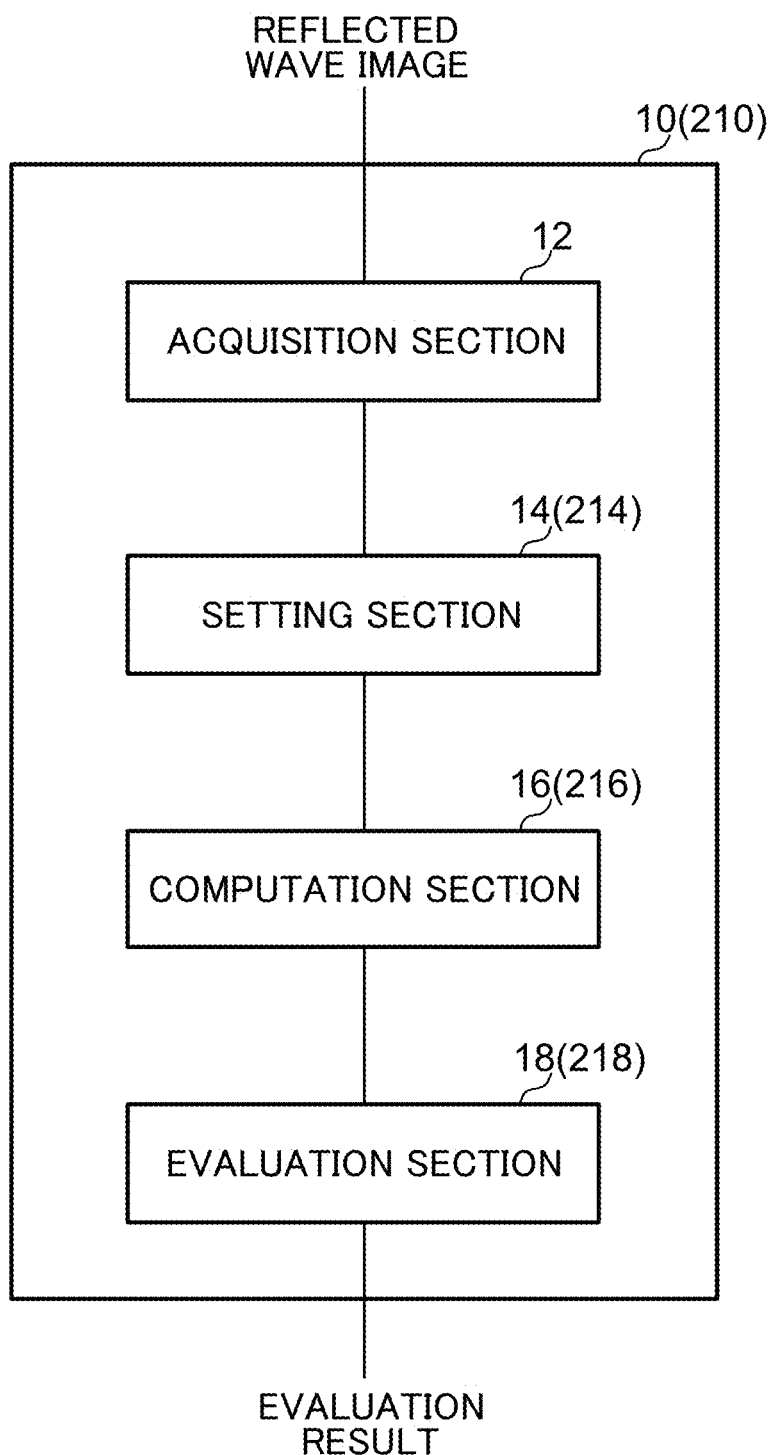
FIG. 6 is a block diagram illustrating an example of functional configuration of a reinforced concrete structure evaluation device.

FIG. 6 is a block diagram illustrating an example of functional configuration of the reinforced concrete structure evaluation device 10. As illustrated in FIG. 6, the reinforced concrete structure evaluation device 10 includes an acquisition section 12, a setting section 14, a computation section 16, and an evaluation section 18 as functional configurations. Each of these functional configurations is implemented by the CPU 42 reading the reinforced concrete structure evaluation program stored in the storage device 46, and expanding and executing this program in the memory 44.

Figure 7:
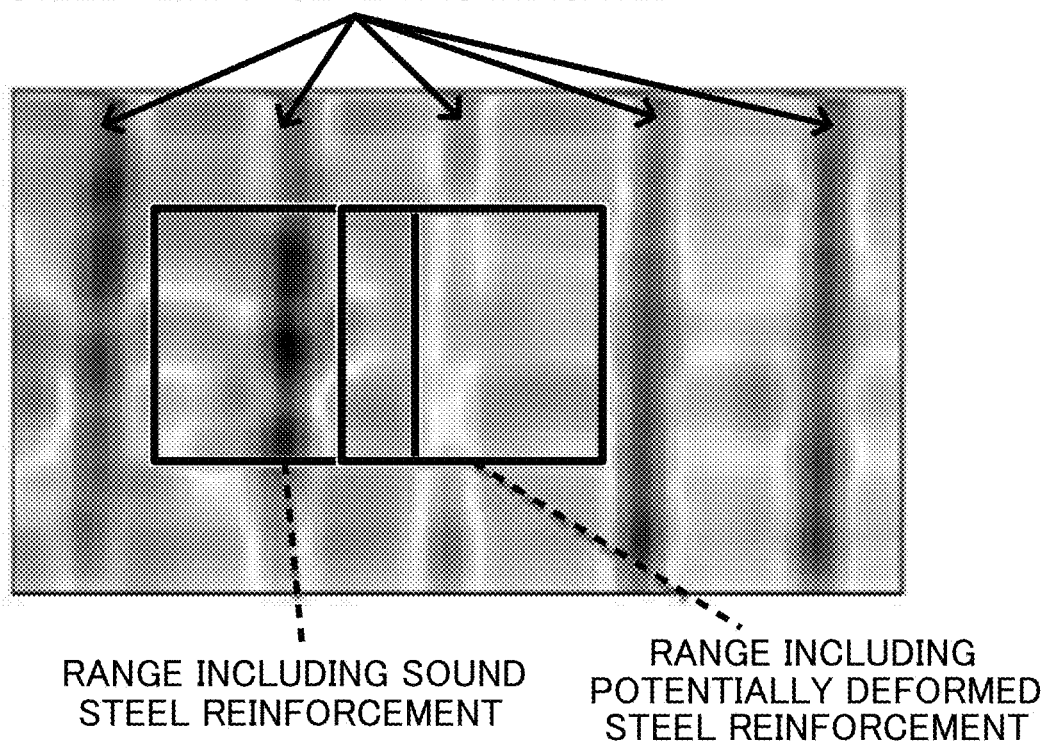
FIG. 7 is a diagram to explain setting of evaluation ranges in a first exemplary embodiment.

As illustrated in FIG. 7, the first exemplary embodiment exploits the fact that in reflected wave intensity images, differences in pixel value variation arise between ranges including sound steel reinforcement portions and portions other than steel reinforcement, and ranges including potentially deformed steel reinforcement and portions other than steel reinforcement. This variation in the pixel values of pixels occupying fixed areas within the reflected wave intensity image is employed to evaluate a degree of deterioration. Detailed explanation follows regarding each functional section.

The acquisition section 12 acquires reflected wave intensity images output from the image processing device 30, and passes the reflected wave intensity images to the setting section 14.

The setting section 14 sets the aforementioned fixed areas in the reflected wave intensity image passed from the acquisition section 12 as evaluation ranges. In the first exemplary embodiment, for each of the evaluation ranges within the reflected wave intensity image, the setting section 14 sets a range that includes both a region at which the presence of steel reinforcement is indicated and a region at which the presence of steel reinforcement is not indicated. When setting plural of such evaluation ranges, the setting section 14 sets the plural evaluation ranges such that the regions at which the presence of steel reinforcement is indicated and the regions at which the presence of steel reinforcement is not indicated are in uniform proportions to each other in each of the plural evaluation ranges. Note that setting plural evaluation ranges in the reflected wave intensity image based on a grid pattern with one side aligned with a direction running along a region at which the presence of steel reinforcement is indicated enables the plural evaluation ranges to be set efficiently.

Figure 8:
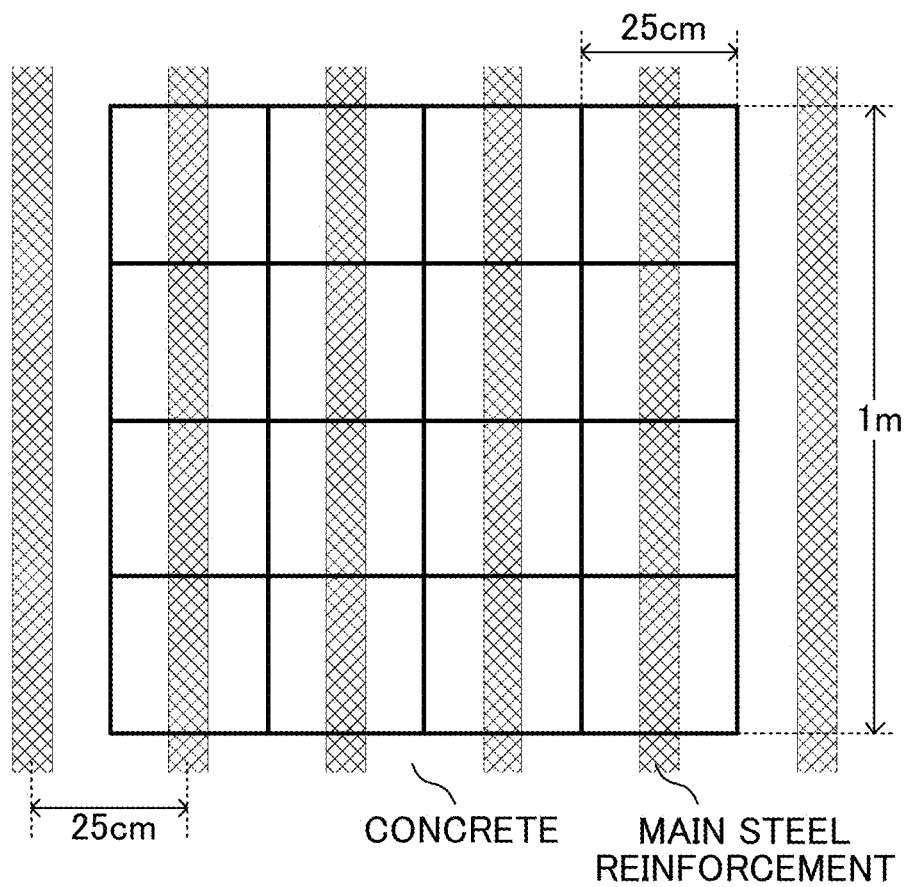
FIG. 8 is a diagram to explain setting of evaluation ranges in the first exemplary embodiment.

As illustrated in FIG. 8, in cases in which plural evaluation ranges are set based on a grid pattern, the ranges may be set such that the grid interval is equal to the interval of the regions at which the presence of steel reinforcement is indicated, and a single grid square corresponds to a single steel reinforcement. For example, in cases in which the steel reinforcement is arranged at a 25 cm pitch, the set ranges are accordingly set to a size corresponding to 25 cm×25 cm in the reflected wave intensity image. Such an approach enables the ranges to be efficiently set such that the proportion of the regions at which the presence of steel reinforcement is indicated with respect to the regions at which the presence of steel reinforcement is not indicated is uniform.

Note that the method for setting the evaluation range is not limited to the example illustrated in FIG. 8 and described above. The evaluation range settings may be adjusted as appropriate, for example such that a single range includes a region at which the presence of two steel reinforcements is indicated.

The setting section 14 may receive setting instructions for the evaluation ranges from a user, or may employ image processing to find locations representing steel reinforcement and set the evaluation ranges automatically.

The computation section 16 computes a statistical indicator of a type set according to the evaluation ranges set by the setting section 14 for the pixel values in the reflected wave intensity image. In the first exemplary embodiment, the computation section 16 computes values representing the variation in pixel values in each of the set evaluation ranges. The values representing the variation in pixel values may, for example, be dispersion or standard deviation values. Explanation follows regarding an example in which standard deviation is employed.

The evaluation section 18 employs the standard deviations of each evaluation range as computed by the computation section 16 to evaluate the degree of deterioration of the reinforced concrete deck. Specifically, in cases in which the steel reinforcement is in a sound condition, the contrast between the region at which the presence of steel reinforcement is indicated and the region at which the presence of steel reinforcement is not indicated in the reflected wave intensity image is greater, namely the standard deviation is greater, than in cases in which the steel reinforcement has deformed (see FIG. 7). This fact is exploited by the evaluation section 18 to evaluate the degree of deterioration of the reinforced concrete deck.

More specifically, the evaluation section 18 is able to make an assessment that deterioration has occurred in an evaluation range in cases in which the standard deviation computed for that evaluation range falls below a predetermined reference value.

Moreover, the evaluation section 18 may evaluate the degree of deterioration of the reinforced concrete deck in blocks, with each block including plural evaluation ranges. For example, as illustrated in FIG. 9, the evaluation section 18 is able to make an assessment that deterioration has occurred in a block (one block being configured by 4×4 evaluation ranges in the example illustrated in FIG. 9) in cases in which the median value of the standard deviations computed for this block falls below a reference value (for example 5.0).

Note that since the appropriate reference value will vary depending on such factors as the individual road bridge and the detection conditions when performing reflected response waveform detection, it may be difficult to set a one-size-fits-all reference value. Accordingly, standard deviations for each evaluation range, as computed from reflected wave intensity images acquired when the reinforced concrete deck is known to be in a sound condition such as after carrying out construction or repair work on the road bridge, are stored as reference values. The evaluation section 18 may then compare the standard deviations for each evaluation range as computed from the reflected wave intensity images acquired when carrying out evaluation against the corresponding reference values in order to evaluate the degree of deterioration of the reinforced concrete deck.

Figure 10:
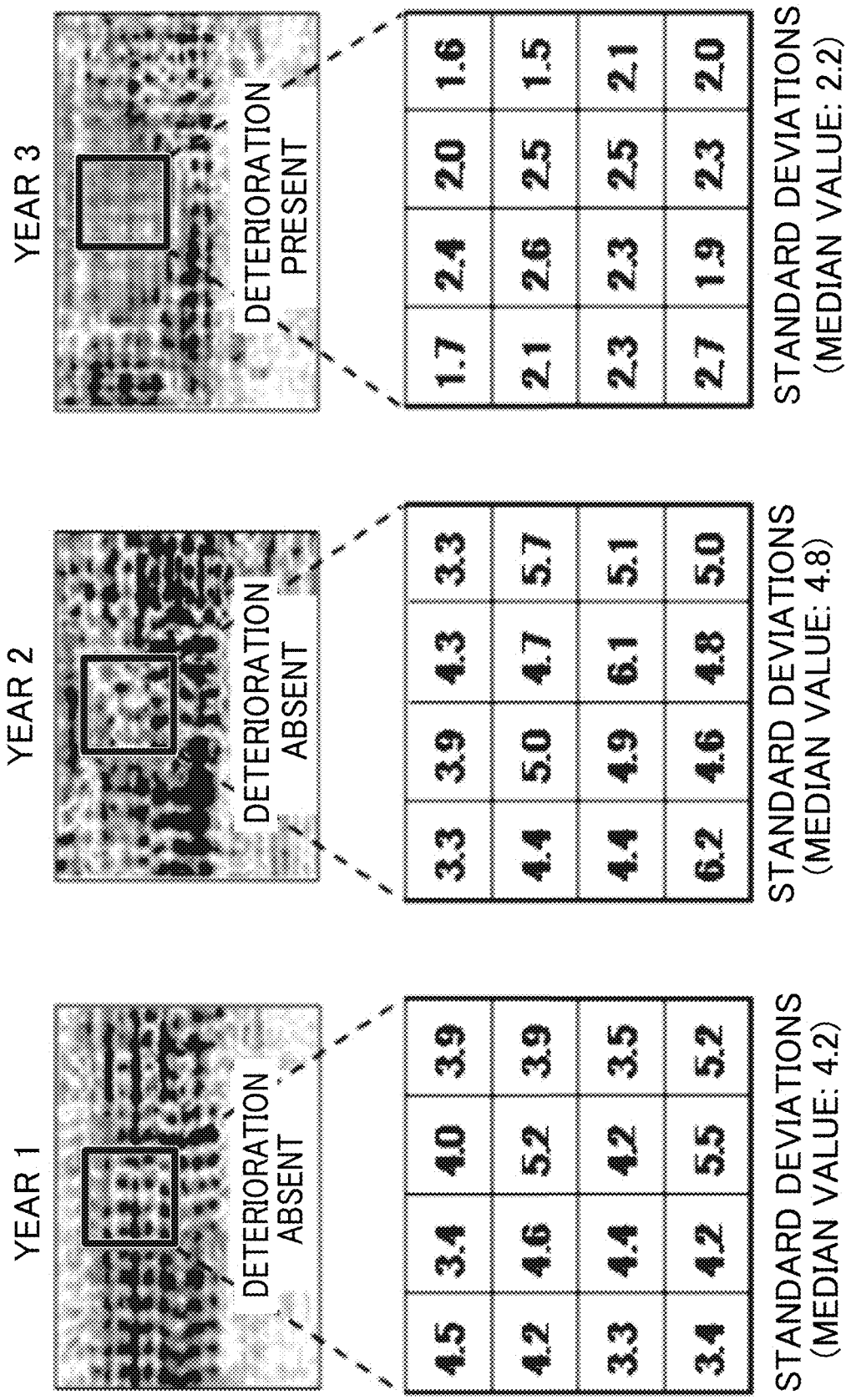
FIG. 10 is a diagram to explain an example of degree of deterioration evaluation employing change over time in standard deviations.

Alternatively, the evaluation section 18 may evaluate change over time in the degree of deterioration by comparing the standard deviations computed by the computation section 16 for each of plural reflected wave intensity images acquired over time at a single location of the reinforced concrete deck. For example, as illustrated in FIG. 10, the evaluation section 18 may evaluate the amount of change on an annual basis by comparing the standard deviations computed for a single location of the reinforced concrete deck against the standard deviations obtained for the same location in previous years. In the example illustrated in FIG. 10, the median value of the standard deviations within a block reveal a marked decline in the third year compared to the first and second years, enabling an assessment to be made that this location of the reinforced concrete deck has suffered from deterioration.

Alternatively, the evaluation section 18 may evaluate the degree of deterioration at a single location not only based on comparisons over time but also based on comparisons of the standard deviations computed by the computation section 16 for each of plural reflected wave intensity images acquired at different locations of the reinforced concrete deck.

Next, explanation follows regarding operation of the reinforced concrete structure evaluation system 100 according to the first exemplary embodiment.

The electromagnetic wave device 20 detects a reflected response waveform for each grid square of the reflected wave intensity detection range 95 as the vehicle 90 travels across the road bridge. The reflected response waveforms detected by the electromagnetic wave device 20 are input to the image processing device 30, and the image processing device 30 generates reflected wave intensity images based on the reflected response waveforms for the respective grid squares.

Figure 11:
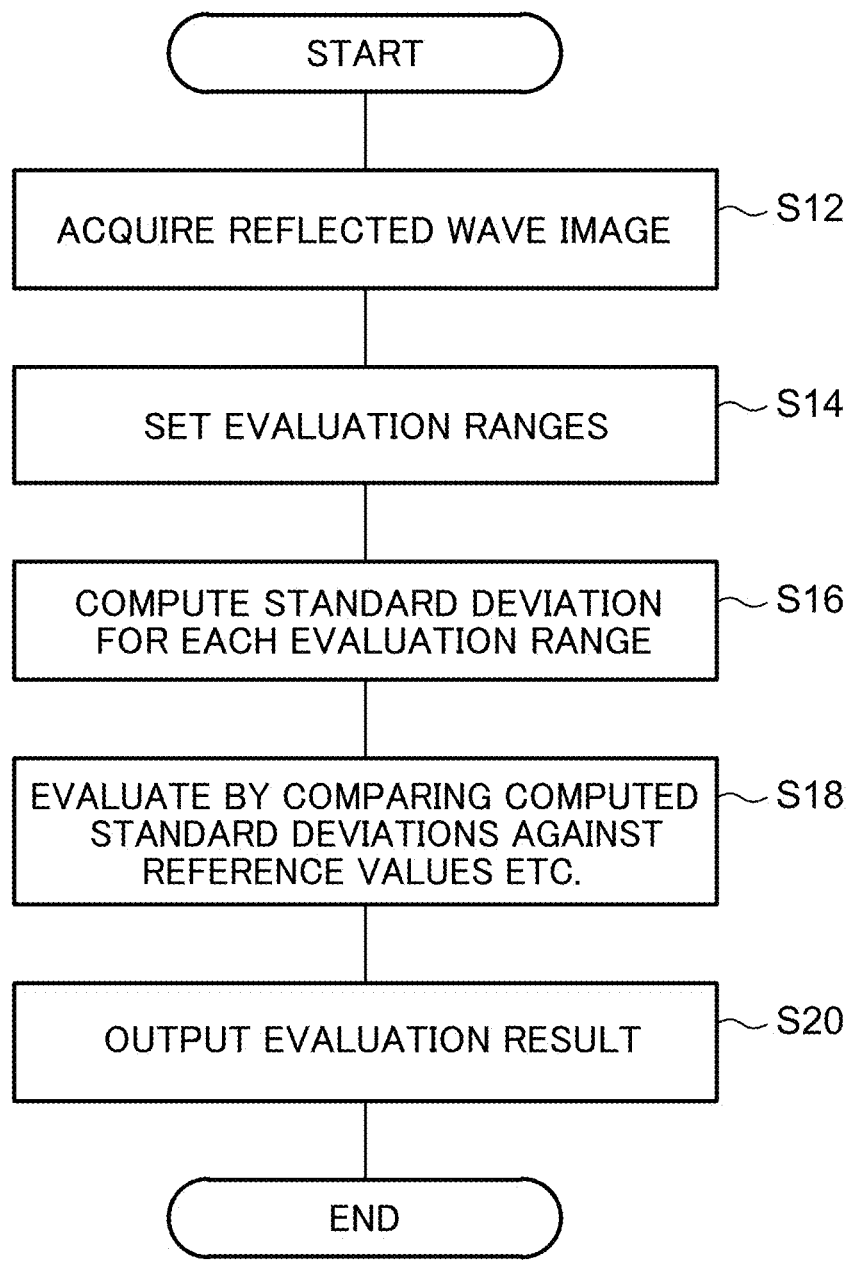
FIG. 11 is a flowchart illustrating an example of reinforced concrete structure evaluation processing.

When the reflected wave intensity images generated by the image processing device 30 are input to the reinforced concrete structure evaluation device 10, the reinforced concrete structure evaluation device 10 executes the reinforced concrete structure evaluation processing illustrated in FIG. 11. FIG. 11 is a flowchart illustrating a flow of reinforced concrete structure evaluation processing executed by the CPU 42 of the reinforced concrete structure evaluation device 10. The CPU 42 reads the reinforced concrete structure evaluation program from the storage device 46 and expands and executes the program in the memory 44, such that the CPU 42 functions as the respective functional configurations of the reinforced concrete structure evaluation device 10 in order to execute the reinforced concrete structure evaluation processing illustrated in FIG. 11.

At step S12, the acquisition section 12 acquires an input reflected wave intensity image and passes the reflected wave intensity image to the setting section 14.

Next, at step S14, the setting section 14 sets evaluation ranges in the reflected wave intensity image received from the acquisition section 12.

Next, at step S16, for each of the set evaluation ranges the computation section 16 computes the standard deviation of the pixel values of the pixels included in the evaluation range.

Next, at step S18, the evaluation section 18 compares the standard deviations of each evaluation range as computed by the computation section 16 against a predetermined reference value, a standard deviation obtained under sound conditions, a standard deviation obtained in the past, a standard deviation obtained for another location, or the like in order to evaluate the degree of deterioration of the reinforced concrete deck.

Next, at step S20, the evaluation section 18 outputs an evaluation result, and the reinforced concrete structure evaluation processing is ended.

As described above, according to the reinforced concrete structure evaluation system of the first exemplary embodiment, the reinforced concrete structure evaluation device computes values such as standard deviations representing the variation in pixel values in each range in a reflected wave intensity image generated from reflected waves from electromagnetic waves radiated into a reinforced concrete deck, each of these ranges including a region at which the presence of steel reinforcement is indicated and a region at which the presence of steel reinforcement is not indicated, and employs these computed values to evaluate the degree of deterioration of the reinforced concrete deck interior. This enables the degree of deterioration of the reinforced concrete deck interior to be quantitatively evaluated.

Setting the ranges for which the values representing the variation in pixel values are computed based on a grid pattern with a grid interval equal to the interval of the steel reinforcements enables efficient range setting in which the region at which the presence of steel reinforcement is indicated and the region at which the presence of steel reinforcement is not indicated in each range are in uniform proportions to each other.

Moreover, comparing against values such as standard deviations for the same location of the reinforced concrete deck over time and comparing different locations against each other enables the degree of deterioration of the reinforced concrete deck interior to be quantitatively evaluated even in cases in which it is difficult to set a one-size-fits-all reference value.

Second Exemplary Embodiment

Next, explanation follows regarding a second exemplary embodiment. In the second exemplary embodiment, explanation follows regarding a case in which the set evaluation ranges differ from those of the first exemplary embodiment, and the type of statistical indicator computed for the evaluation ranges therefore also differs. Note that configurations of a reinforced concrete structure evaluation system according to the second exemplary embodiment that are similar to those of the reinforced concrete structure evaluation system 100 according to the first exemplary embodiment are allocated the same reference numerals as in the first exemplary embodiment, and detailed explanation thereof is omitted.

As illustrated in FIG. 1, a reinforced concrete structure evaluation system 200 according to the second exemplary embodiment is configured including a reinforced concrete structure evaluation device 210, an electromagnetic wave device 20, and an image processing device 30.

As illustrated in FIG. 6, the reinforced concrete structure evaluation device 210 includes an acquisition section 12, a setting section 214, a computation section 216, and an evaluation section 218 as functional configurations.

Figure 12:
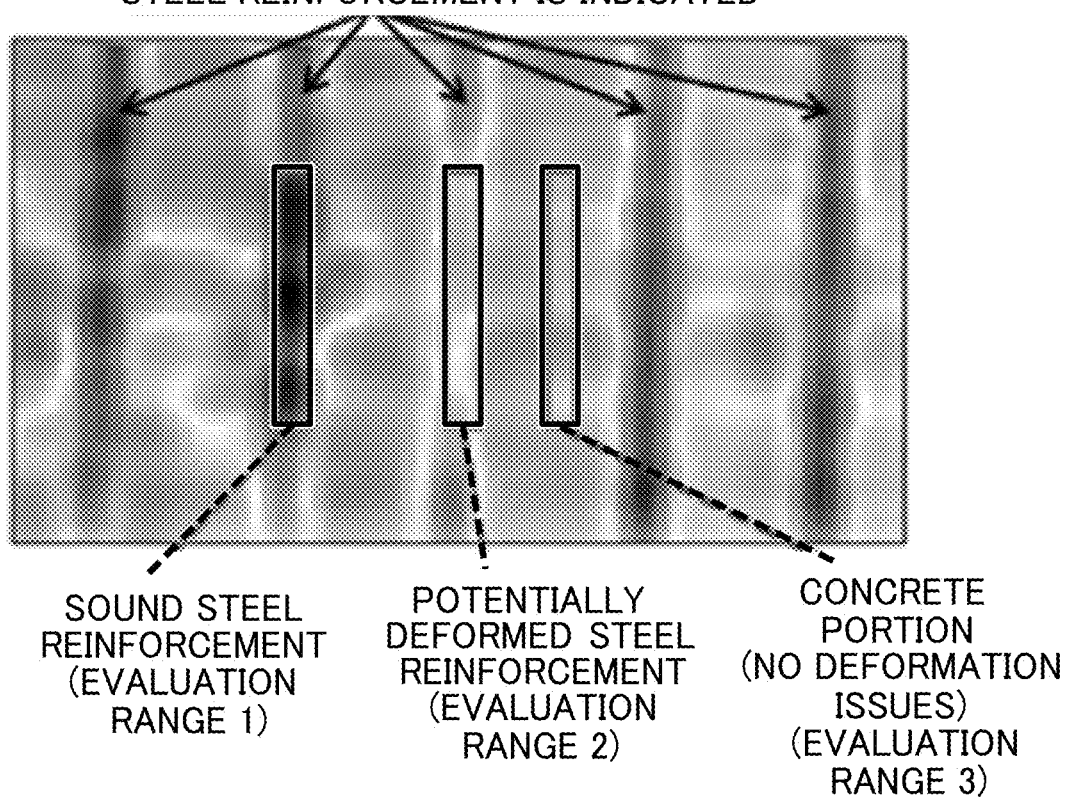
FIG. 12 is a diagram to explain setting of evaluation ranges in a second exemplary embodiment.

As illustrated in FIG. 12, the second exemplary embodiment exploits the fact that pixel values in the reflected wave intensity images exhibit certain characteristics depending on whether they correspond to portions representing steel reinforcement or portions representing concrete, or sound portions or potentially deformed portions. These characteristics are employed when setting evaluation ranges and computing statistical indicators.

The setting section 214 sets evaluation ranges deemed to include only regions at which the presence of steel reinforcement is indicated or sets evaluation ranges deemed to include only regions at which the presence of steel reinforcement is not indicated in the reflected wave intensity images received from the acquisition section 12. Similarly to the setting section 14 of the first exemplary embodiment, the setting section 214 may receive setting instructions for the evaluation ranges from a user, or may employ image processing to find locations representing steel reinforcement and set the evaluation ranges automatically.

Note that both in cases in which user instructions are employed and cases in which image processing is employed, it is difficult to accurately identify boundaries between steel reinforcement portions and concrete portions. Accordingly, regions at which the presence of steel reinforcement is indicated are identified in the reflected wave intensity image based on information regarding a region at which the presence of steel reinforcement is indicated as found through image processing and information such as the width of and interval between the actual steel reinforcements. Then, when setting evaluation ranges deemed to include only regions at which the presence of steel reinforcement is indicated, in cases in which a region at which the presence of steel reinforcement is indicated identified as described above makes up at least a predetermined proportion (for example at least 90%) of an evaluation range, that evaluation range is deemed to be an evaluation range including only a region at which the presence of steel reinforcement is indicated. Similarly, when setting evaluation ranges deemed to include only regions at which the presence of steel reinforcement is not indicated, in cases in which a region at which the presence of steel reinforcement is indicated identified as described above makes up a proportion of an evaluation range no greater than a predetermined proportion (for example no greater than 10%), that evaluation range is deemed to be an evaluation range including only regions at which the presence of steel reinforcement is not indicated.

The computation section 216 computes standard deviations and average pixel values as statistical indicators for each of the evaluation ranges set by the setting section 214. Note that standard deviations are an example of values representing a variation in pixel values.

Here, an example is used of standard deviations and average values for evaluation ranges deemed to include only regions at which the presence of steel reinforcement is indicated (referred to hereafter as "steel reinforcement portion evaluation ranges") and evaluation ranges deemed to include only regions at which the presence of steel reinforcement is not indicated (i.e. concrete; referred to hereafter as "concrete portion evaluation ranges") under various conditions.

In the following example, an evaluation range 1, an evaluation range 2, and an evaluation range 3 are set as steel reinforcement portion evaluation ranges as illustrated in FIG. 12. The evaluation range 1 is a portion representing sound steel reinforcement (referred to hereafter as a "sound steel reinforcement location"), the evaluation range 2 is a portion representing potentially deformed steel reinforcement (referred to hereafter as a "corroded steel reinforcement location"), and the evaluation range 3 is a portion representing a concrete portion without deformation issues (referred to hereafter as a "sound concrete location"). The respective evaluation ranges are regions of a reflected wave intensity image, each corresponding to an actual size of 3 cm×25 cm.

Figure 13:
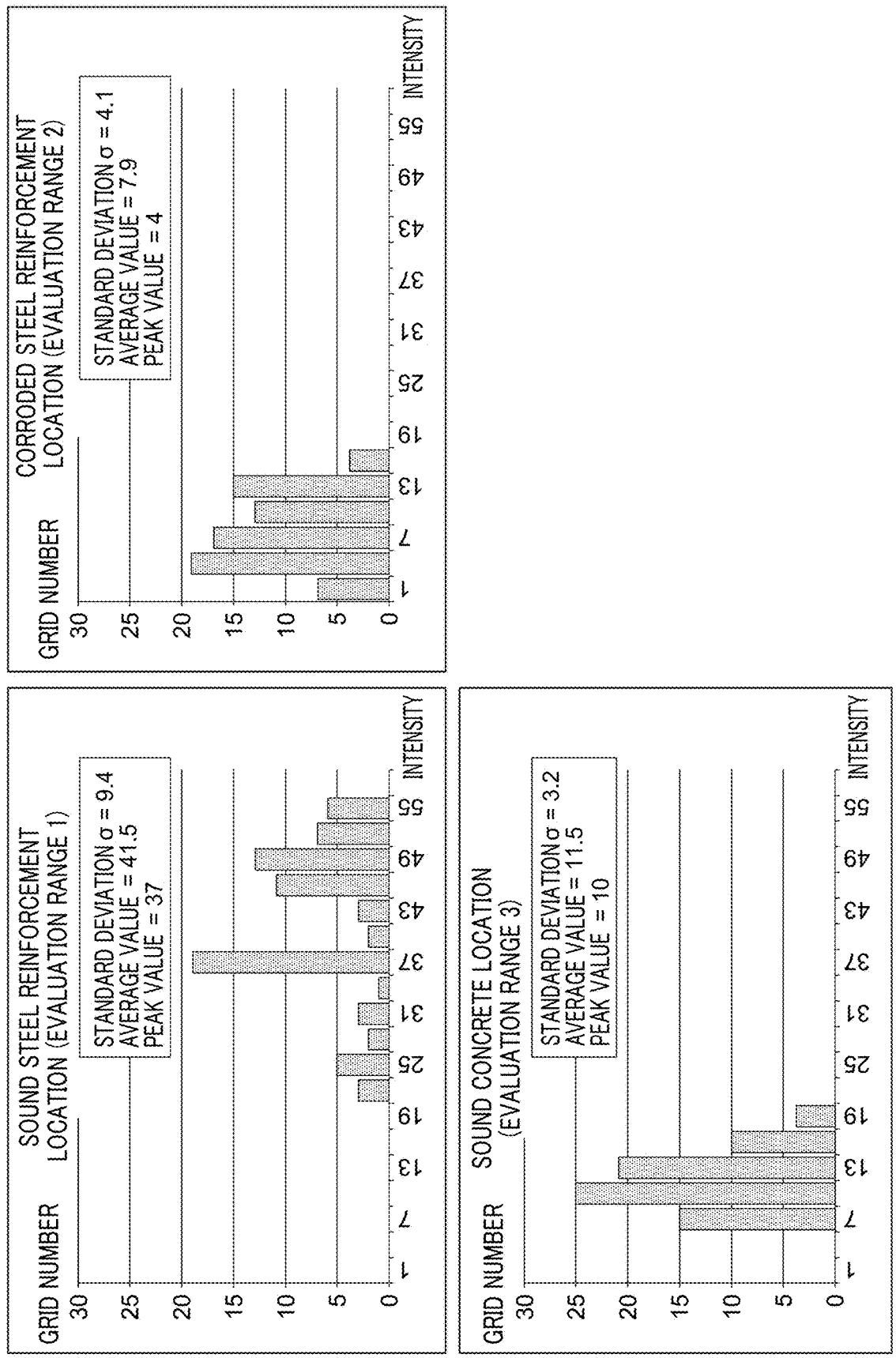
FIG. 13 is a diagram illustrating respective pixel value distributions in evaluation ranges corresponding to a sound steel reinforcement location, a corroded steel reinforcement location, and a sound concrete location.

FIG. 13 illustrates pixel value distributions corresponding to each evaluation range. In FIG. 13, "intensity" refers to the reflected wave intensity and corresponds to the pixel values in the reflected wave intensity image, and "grid number" corresponds to the number of pixels. Similar also applies in subsequent drawings. As illustrated in FIG. 13, the sound steel reinforcement location exhibits a greater variation in pixel values and a distribution of pixel values that tends toward higher reflected wave intensities than the sound concrete location. Moreover, the corroded steel reinforcement location exhibits a tendency toward less variation in pixel values and a distribution of pixel values that tends lower reflected wave intensities than the sound steel reinforcement location.

FIG. 14 illustrates standard deviations and average values of pixel values for each of the evaluation ranges, as obtained from the pixel value distributions illustrated in FIG. 13. It can be seen that the characteristics described above are quantitatively expressed by the standard deviations and average values.

Figure 15:
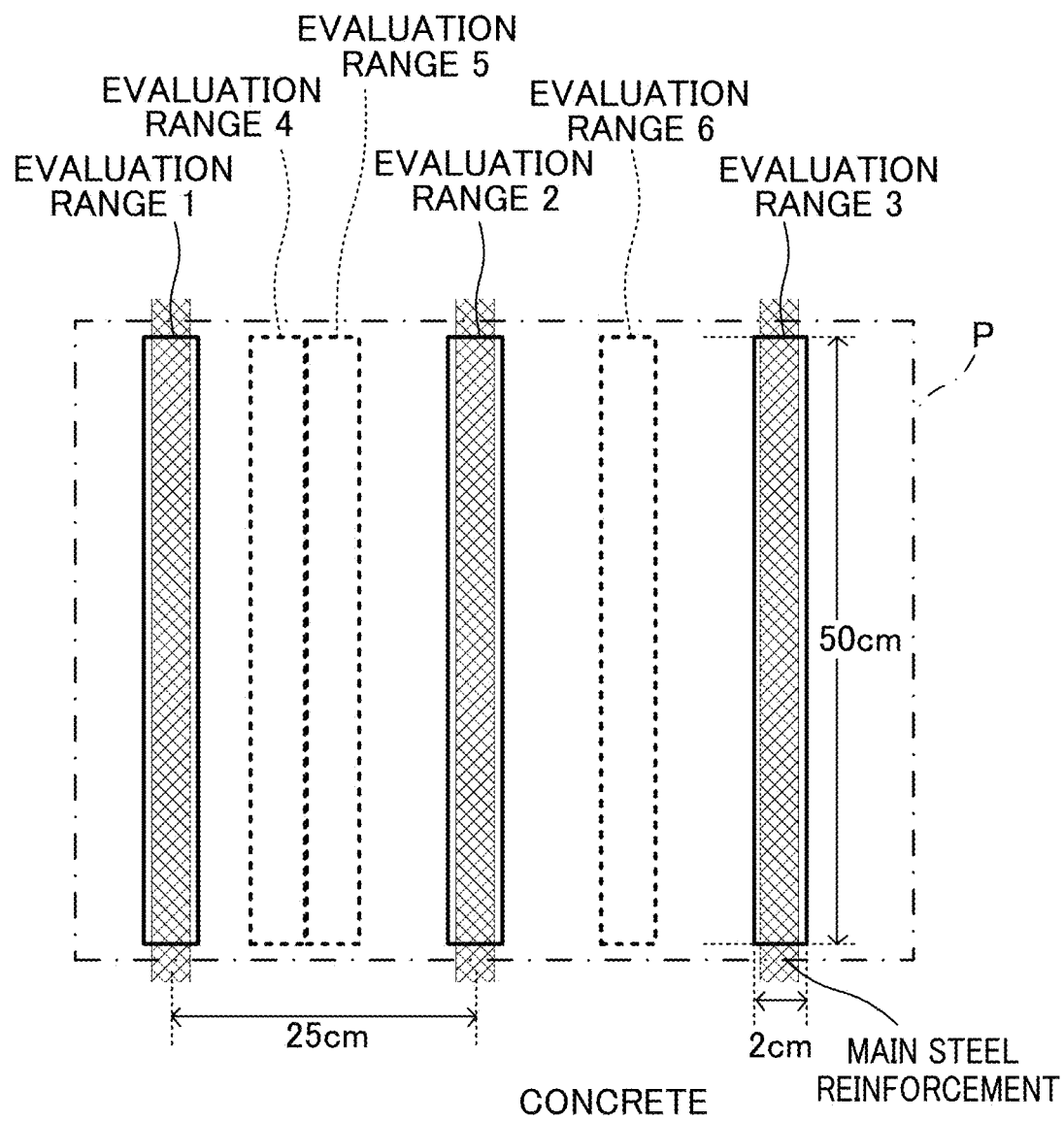
FIG. 15 is a diagram to explain an example of setting of evaluation ranges in the second exemplary embodiment.

Explanation follows regarding another example in which, as illustrated in FIG. 15, evaluation ranges 1 to 3 are set as evaluation ranges for steel reinforcement portions, and evaluation ranges 4 to 6 are set as evaluation ranges for concrete portions. The respective evaluation ranges are regions in a reflected wave intensity image, each corresponding to an actual size of 2 cm×50 cm.

Figure 16:
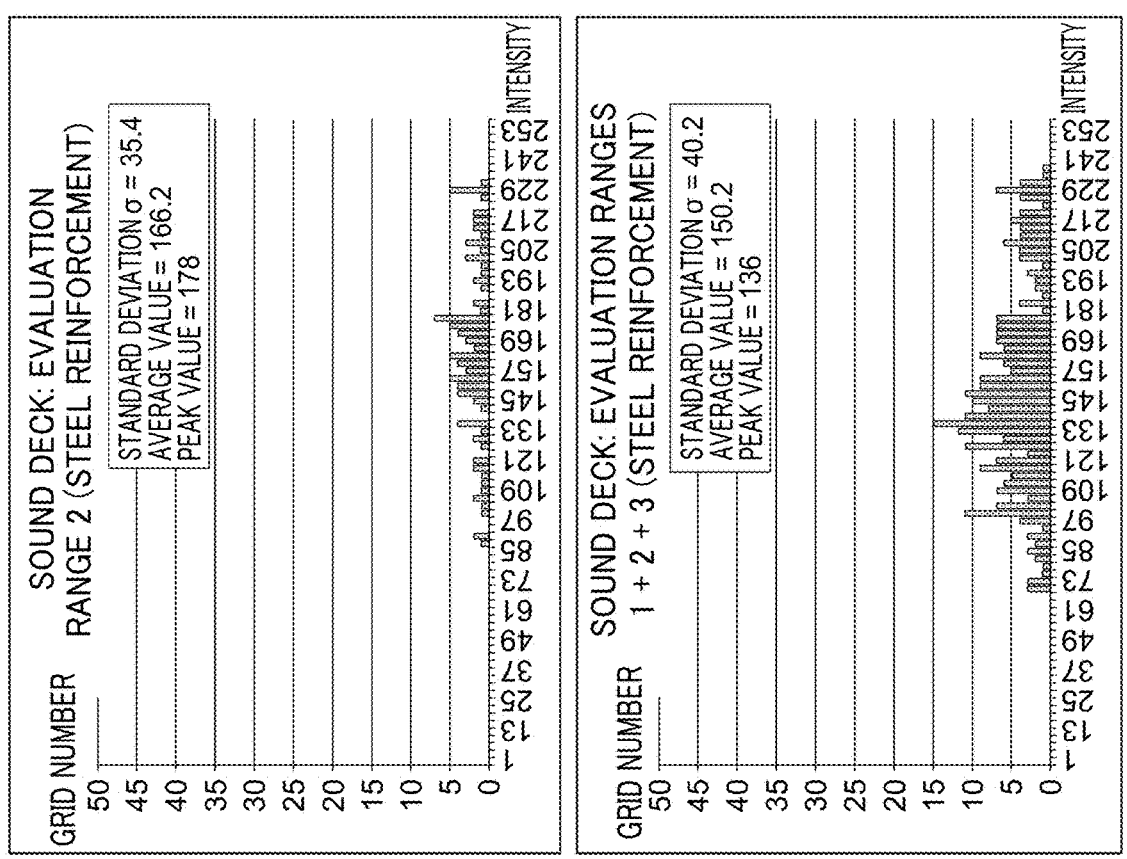
FIG. 16 is a diagram illustrating pixel value distributions in evaluation ranges corresponding to steel reinforcement portions in a sound deck.

FIG. 16 illustrates pixel value distributions corresponding to respective steel reinforcement portion evaluation ranges in a sound reinforced concrete deck (referred to hereafter as a "sound deck"). Similarly, FIG. 17 illustrates pixel value distributions corresponding to respective concrete portion evaluation ranges in the sound deck. When FIG. 16 and FIG. 17 are compared, the steel reinforcement portions of the sound deck exhibit a greater variation in pixel values and a distribution in which more of the pixel values tend toward higher reflected wave intensities than the concrete portions of the sound deck.

FIG. 18 illustrates standard deviations and average values for pixel values of each of the evaluation ranges, as obtained from the pixel value distributions illustrated in FIG. 16 and FIG. 17. It can be seen that the characteristics described above are quantitatively expressed by the standard deviations and average values.

Figure 19:
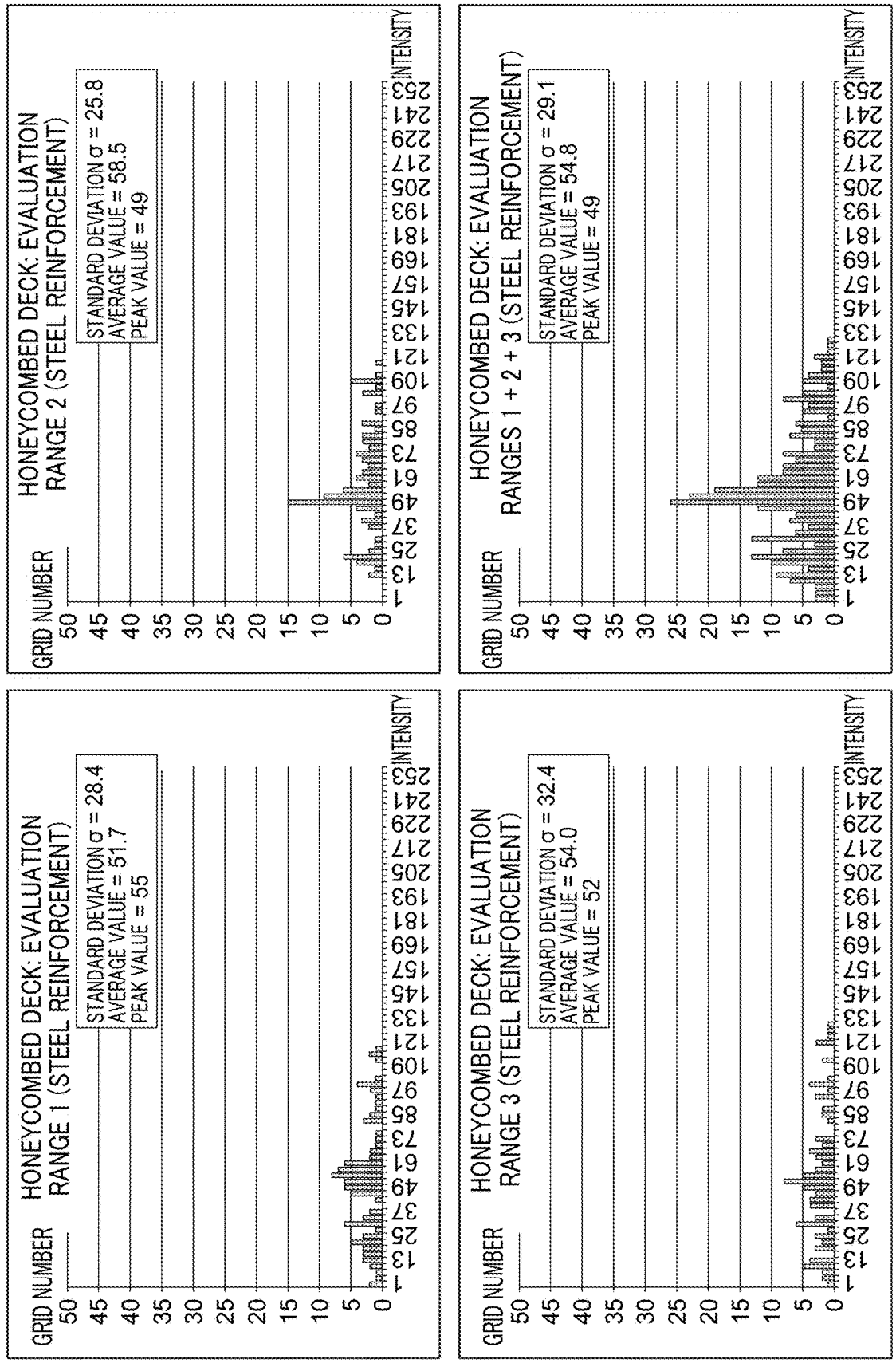
FIG. 19 is a diagram illustrating pixel value distributions in evaluation ranges corresponding to steel reinforcement portions in a honeycombed deck.
Figure 20:
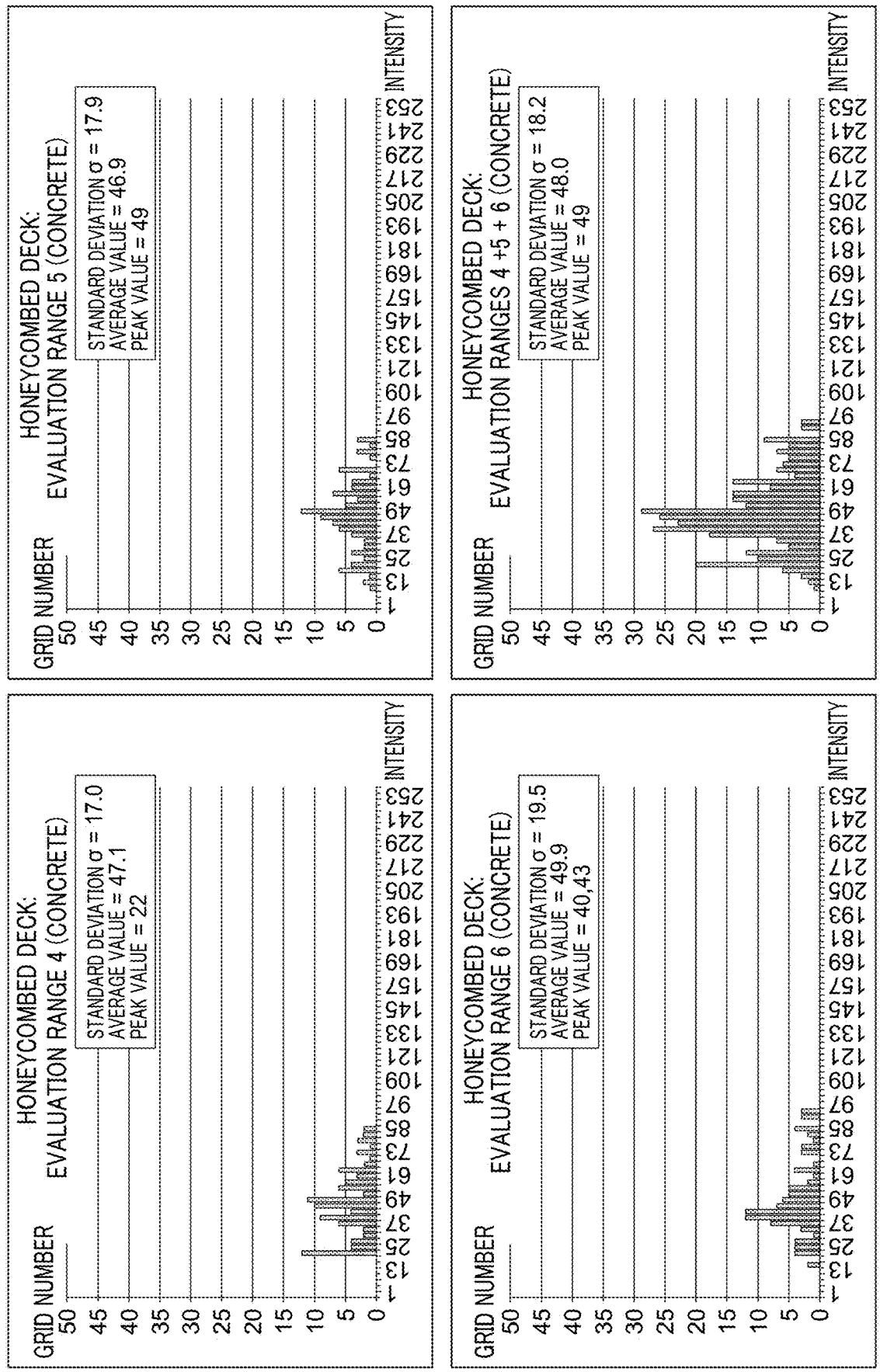
FIG. 20 is a diagram illustrating pixel value distributions in evaluation ranges corresponding to concrete portions in a honeycombed deck.

Moreover, FIG. 19 illustrates pixel value distributions corresponding to respective steel reinforcement portion evaluation ranges in a reinforced concrete deck with simulated concrete honeycombing at the portion indicated by the single-dotted dashed lines P in FIG. 15 (referred to hereafter as "honeycombed deck"). Similarly, FIG. 20 illustrates pixel value distributions corresponding to respective concrete portion evaluation ranges in the honeycombed deck.

Figure 21:
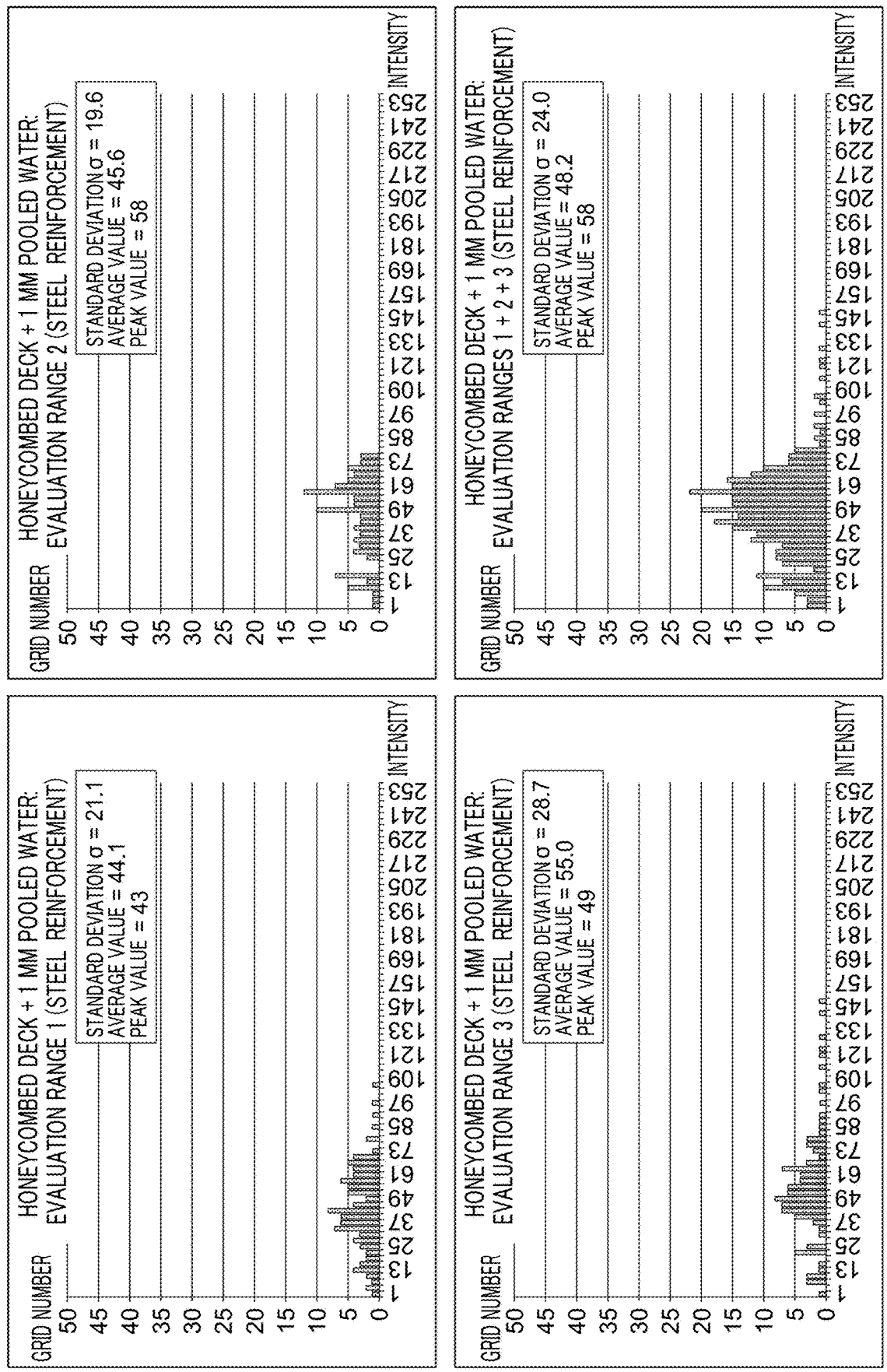
FIG. 21 is a diagram illustrating pixel value distributions in evaluation ranges corresponding to steel reinforcement portions in a honeycombed deck with 1 mm of pooled water.
Figure 22:
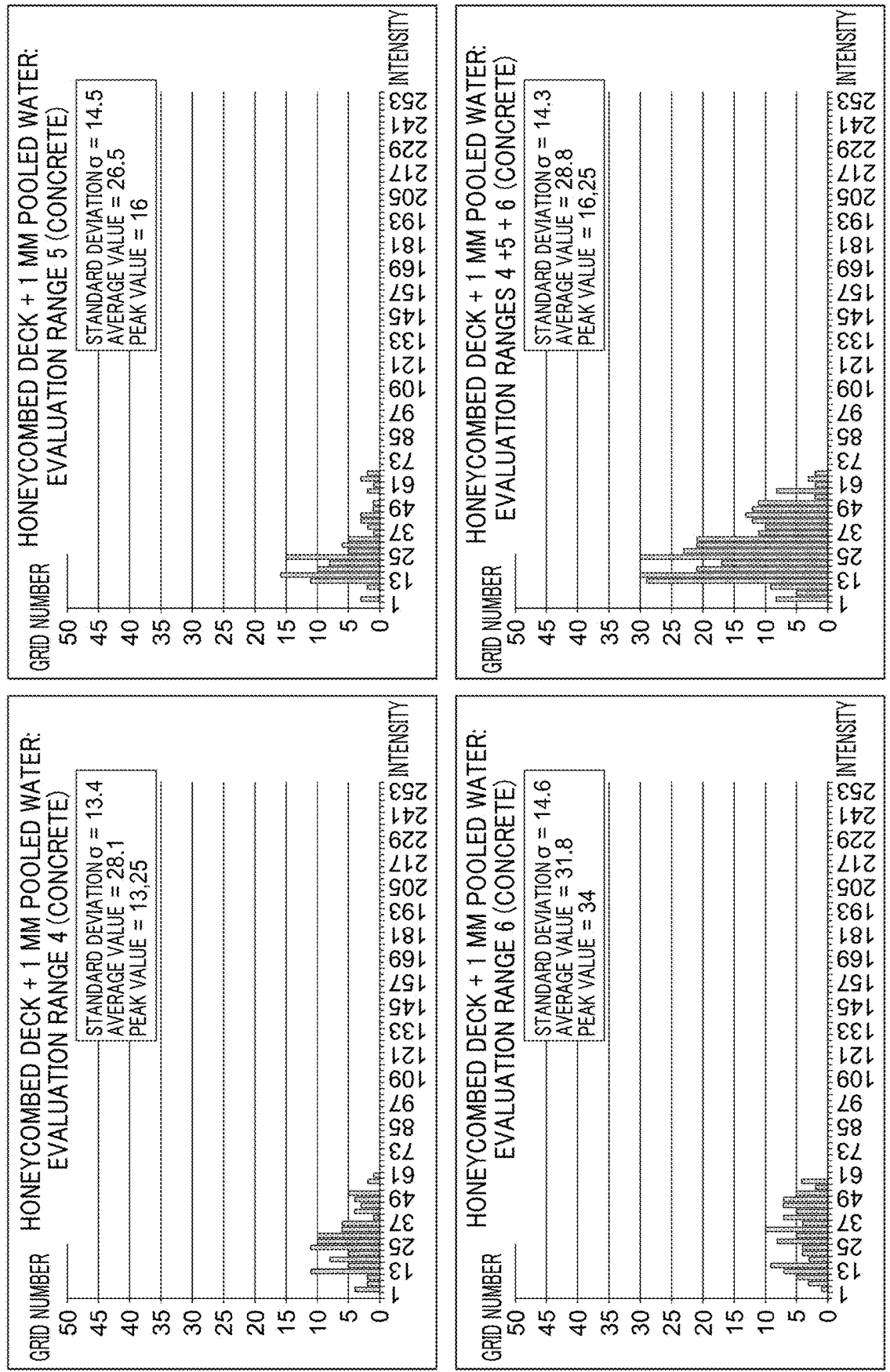
FIG. 22 is a diagram illustrating pixel value distributions in evaluation ranges corresponding to concrete portions in a honeycombed deck with 1 mm of pooled water.
Figure 23:
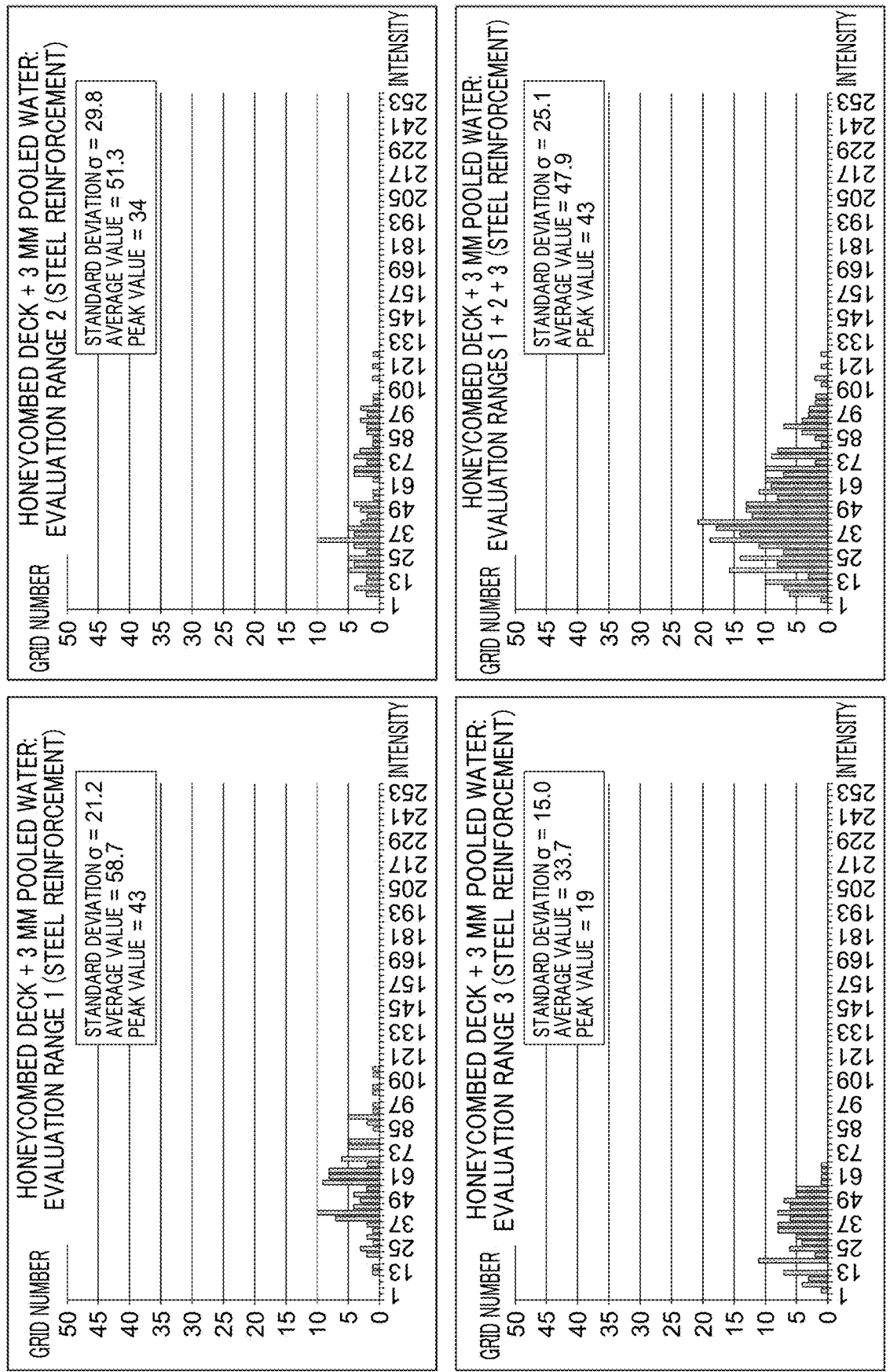
FIG. 23 is a diagram illustrating pixel value distributions in evaluation ranges corresponding to steel reinforcement portions in a honeycombed deck with 3 mm of pooled water.
Figure 24:
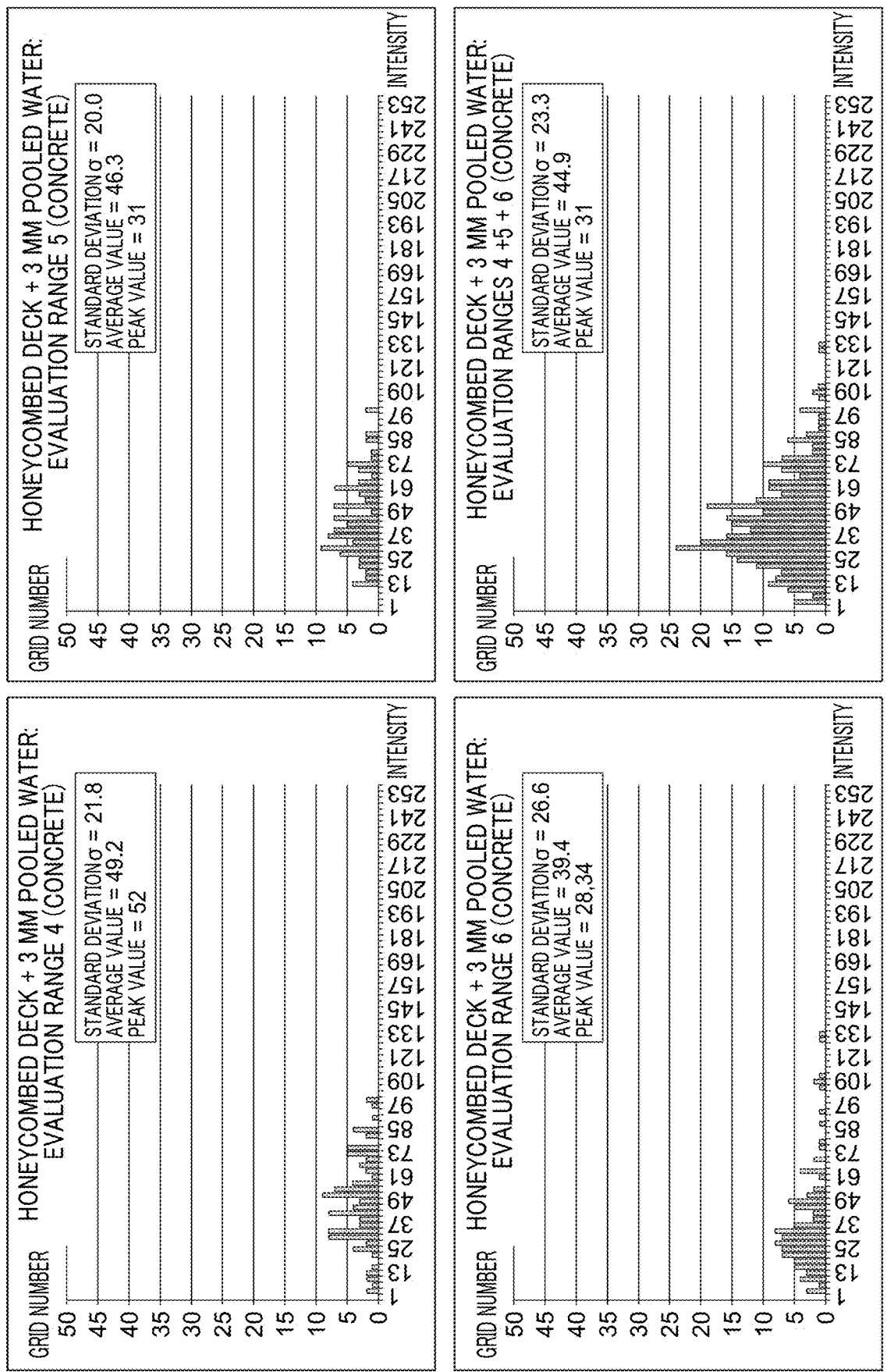
FIG. 24 is a diagram illustrating pixel value distributions in evaluation ranges corresponding to concrete portions in a honeycombed deck with 3 mm of pooled water.

FIG. 21 illustrates pixel value distributions corresponding to respective steel reinforcement portion evaluation ranges in a reinforced concrete deck with simulated concrete honeycombing and 1 mm of pooled water at the portion indicated by the single-dotted dashed lines P in FIG. 15 (referred to hereafter as "honeycombed+1 mm deck"). Similarly, FIG. 22 illustrates pixel value distributions corresponding to respective concrete portion evaluation ranges in the honeycombed+1 mm deck. FIG. 23 illustrates pixel value distributions corresponding to respective steel reinforcement portion evaluation ranges in a reinforced concrete deck with simulated concrete honeycombing and 3 mm of pooled water at the portion indicated by the single-dotted dashed lines P in FIG. 15 (referred to hereafter as "honeycombed+3 mm deck"). Similarly, FIG. 24 illustrates pixel value distributions corresponding to respective concrete portion evaluation ranges in the honeycombed+3 mm deck.

As illustrated in FIG. 19 to FIG. 24, in cases in which concrete portions have deformation issues, a slight shift in pixel values toward lower reflected wave intensities is exhibited in comparison to the concrete portions of the sound deck.

FIG. 25 illustrates standard deviations and average values for the pixel values in each of the evaluation ranges, as obtained from the pixel value distributions illustrated in FIG. 19 to FIG. 24. It can be seen that the characteristics described above are quantitatively expressed by the average values.

Similarly to the evaluation section 18 according to the first exemplary embodiment, the evaluation section 218 employs the standard deviations and average values computed by the computation section 216 to evaluate the degree of deterioration of the reinforced concrete structure based on the quantitative characteristics of standard deviations and average values as described above.

Since a hardware configuration of the reinforced concrete structure evaluation device 210 according to the second exemplary embodiment is similar to the hardware configuration of the reinforced concrete structure evaluation device 10 according to the first exemplary embodiment illustrated in FIG. 5, explanation thereof is omitted.

Next, explanation follows regarding operation of the reinforced concrete structure evaluation system 200 according to the second exemplary embodiment. In the second exemplary embodiment, the reinforced concrete structure evaluation device 210 executes the reinforced concrete structure evaluation processing illustrated in FIG. 11.

Note that unlike in the first exemplary embodiment, at step S14 the setting section 214 sets steel reinforcement portion evaluation ranges and concrete portion evaluation ranges. Furthermore, at step S16 the computation section 216 computes for each of the evaluation range a standard deviation and average value of the pixel values in the evaluation range.

As described above, according to the reinforced concrete structure evaluation system in the second exemplary embodiment, the reinforced concrete structure evaluation device computes values such as average values and standard deviations representing the variation in pixel values in each range in a reflected wave intensity image generated from reflected waves from electromagnetic waves radiated into a reinforced concrete deck, each of these ranges being either a range deemed to include only regions at which the presence of steel reinforcement is indicated or a range deemed to include only regions at which the presence of steel reinforcement is not indicated, and employs these computed values to evaluate the degree of deterioration of the reinforced concrete deck interior. This enables the degree of deterioration of the reinforced concrete deck interior to be quantitatively evaluated.

Note that although in the first exemplary embodiment explanation has been given regarding a case in which evaluation ranges are set such that each evaluation range includes a region at which the presence of steel reinforcement is indicated and a region at which the presence of steel reinforcement is not indicated, and evaluation is performed using values representing the variation in pixel values, such as the standard deviations of the evaluation ranges, this approach makes the assumptions that the region at which the presence of steel reinforcement is not indicated, namely the concrete portion, is sound, and that a large contrast will be exhibited between the steel reinforcement portion and the concrete portion. However, in reality, there is no guarantee that acquired reflected wave intensity images will include a sound concrete portion, and cases also arise in which there is little contrast between the concrete portion and the steel reinforcement portion even when the steel reinforcement portion is sound.

Accordingly, in cases in which definitive evaluation results cannot be obtained using the methodology of the first exemplary embodiment, the methodology of the second exemplary embodiment may be applied to locations configuring evaluation ranges set using the methodology of the first exemplary embodiment in order to set steel reinforcement portion evaluation ranges and concrete portion evaluation ranges and perform evaluation thereon.

Moreover, cases also arise in which differences between values that are due to differences in conditions and position are not clear from the values representing the variation in pixel values, such as standard deviations, or the average values for the steel reinforcement portion evaluation ranges and the concrete portion evaluation ranges set as in the second exemplary embodiment. For example, as illustrated in FIG. 12, cases arise in which there is little difference between the pixel values, namely the reflected wave intensity, in the reflected wave intensity image between steel reinforcement portions that are potentially deformed due to deterioration, and concrete portions. It is therefore difficult to evaluate such evaluation ranges using standard deviations and average values.

Accordingly, in cases in which definitive evaluation results cannot be obtained using the methodology of the second exemplary embodiment, the methodology of the first exemplary embodiment may be applied to locations configuring evaluation ranges set using the methodology of the second exemplary embodiment in order to set evaluation ranges including both steel reinforcement portions and concrete portions and perform evaluation thereon.

Combining the methodology of the first exemplary embodiment and the methodology of the second exemplary embodiment as described above enables more precise and detailed evaluation to be performed.

Note that in the respective exemplary embodiments described above, explanation has been given regarding cases in which evaluation is performed on a reinforced concrete deck configuring a road surface structure of a road bridge. However, there is no limitation thereto, and the technology disclosed herein may be applied to other reinforced concrete structures.

Moreover, in the exemplary embodiments described above, explanation has been given regarding cases in which the image processing device and the reinforced concrete structure evaluation device are provided in a vehicle to which the electromagnetic wave device is attached. However, there is no limitation thereto, and the image processing device and the reinforced concrete structure evaluation device may be configured by devices external to the vehicle. In such cases, information regarding the reflected response waveforms detected by the electromagnetic wave device may be exchanged between the electromagnetic wave device and the image processing device using wireless communication or the like.

Moreover, although the exemplary embodiments described above have described cases in which the image processing device and the reinforced concrete structure evaluation device are configured by separate devices, the image processing device and the reinforced concrete structure evaluation device may be configured by a single computer.

Note that the parameter setting processing executed by the CPU reading and executing software (a program) in the above exemplary embodiment may be executed by various types of processor other than a CPU. Such processors include programmable logic devices (PLD) that allow circuit configuration to be modified post-manufacture, such as a field-programmable gate array (FPGA), and dedicated electric circuits, these being processors including a circuit configuration custom-designed to execute specific processing, such as an application specific integrated circuit (ASIC). The reinforced concrete structure evaluation processing may be executed by any one of these various types of processor, or may be executed by a combination of two or more of the same type or different types of processor (such as plural FPGAs, or a combination of a CPU and an FPGA). The hardware structure of these various types of processors is more specifically an electric circuit combining circuit elements such as semiconductor elements.

Moreover, in the exemplary embodiments described above, explanation has been given regarding implementations in which the reinforced concrete structure evaluation program is stored in advance (installed) in a storage device. However, there is no limitation thereto. For example, the program may be provided in a format recorded on a recording medium such as CD-ROM, digital versatile disc read only memory (DVD-ROM), or universal serial bus (USB) memory. Alternatively, the program may be provided in a format downloadable from an external device over a network.

The disclosure of Japanese Patent Application No. 2019-033202 is incorporated in its entirety by reference herein.

All cited documents, patent applications, and technical standards mentioned in the present specification are incorporated by reference in the present specification to the same extent as if each individual cited document, patent application, or technical standard was specifically and individually indicated to be incorporated by reference.

The invention claimed is:

1. A reinforced concrete structure evaluation device, comprising:
   an acquisition section configured to acquire an image in which a reflected wave intensity, of an electromagnetic wave that has been radiated in a direction through a surface of a reinforced concrete structure toward an interior of the reinforced concrete structure at respective positions on the surface of the reinforced concrete structure, is expressed by pixel values of pixels corresponding to each of the respective positions;
   a setting section configured to set an evaluation target range in the image acquired by the acquisition section;
   a computation section configured to compute a statistical property of the pixel values of the pixels in the evaluation target range, set by the setting section; and
   an evaluation section configured to evaluate a degree of deterioration of the reinforced concrete structure using the statistical property computed by the computation section.

2. The reinforced concrete structure evaluation device of claim 1, wherein:
   the setting section is configured to set a range including a region at which the presence of steel reinforcement is indicated and a region at which the presence of steel reinforcement is not indicated in the image acquired by the acquisition section; and
   the computation section is configured to compute, as the statistical property, a value representing a variation in pixel values in the range.

3. The reinforced concrete structure evaluation device of claim 2, wherein, in a case in which the setting section sets the range for a plurality of locations in the image, the setting section sets a plurality of ranges such that the region at which the presence of steel reinforcement is indicated and the region at which the presence of steel reinforcement is not indicated are uniformly proportionate to each other in each of the plurality of ranges.

4. The reinforced concrete structure evaluation device of claim 2, wherein the setting section is configured to set, in the image, a plurality of ranges in a grid pattern, with one side of the grid pattern aligned with a direction along the region at which the presence of steel reinforcement is indicated.

5. The reinforced concrete structure evaluation device of claim 4, wherein the setting section is configured to set an interval between respective single sides of the ranges in the grid pattern so as to be equal to an interval between regions at which the presence of steel reinforcement is indicated.

6. A reinforced concrete structure evaluation device comprising:
   an acquisition section configured to acquire an image in which a reflected wave intensity, of an electromagnetic wave that has been radiated in a direction through a surface of a reinforced concrete structure toward an interior of the reinforced concrete structure at respective positions on the surface of the reinforced concrete structure, is expressed by pixel values of pixels corresponding to each of the respective positions;
   a setting section configured to set an evaluation target range in the image acquired by the acquisition section;
   a computation section configured to compute a statistical indicator, of a type corresponding to the range set by the setting section, for pixel values in the image; and
   an evaluation section configured to evaluate a degree of deterioration of the reinforced concrete structure using values computed by the computation section;
   wherein:
   the setting section is configured to set a range deemed to include only a region at which the presence of steel reinforcement is indicated, or a range deemed to include only a region at which the presence of steel reinforcement is not indicated, in the image acquired by the acquisition section; and
   the computation section is configured to compute, as the statistical property, a value representing a variation in pixel values in the range and an average value of the pixel values.

7. The reinforced concrete structure evaluation device of claim 1, wherein the evaluation section is configured to evaluate the degree of deterioration by comparing a statistical property value computed by the computation section against a predetermined reference value.

8. The reinforced concrete structure evaluation device of claim 1, wherein the evaluation section is configured to evaluate a change over time in the degree of deterioration by comparing against each other statistical property values computed by the computation section for each of a plurality of images acquired over time for a single location on the reinforced concrete structure.

9. The reinforced concrete structure evaluation device of claim 1, wherein the evaluation section is configured to evaluate the degree of deterioration by comparing against each other statistical property values computed by the computation section for each of a plurality of images acquired for different locations on the reinforced concrete structure.

10. A reinforced concrete structure evaluation method, comprising:
    with an acquisition section, acquiring an image in which a reflected wave intensity, of an electromagnetic wave that has been radiated in a direction through a surface of a reinforced concrete structure toward an interior of the reinforced concrete structure at respective positions on the surface of the reinforced concrete structure, is expressed by pixel values of pixels corresponding to each of the respective positions;
    with a setting section, setting an evaluation target range in the image acquired by the acquisition section;
    with a computation section, computing a statistical property of the pixel values of the pixels in the evaluation target range set by the setting section; and
    with an evaluation section, evaluating a degree of deterioration of the reinforced concrete structure using statistical property values computed by the computation section.

11. A non-transitory recording medium storing a reinforced concrete structure evaluation program, configured to cause a computer to function as the respective sections configuring the reinforced concrete structure evaluation device of claim 10.

* * * * *